(12) United States Patent
Li et al.

(10) Patent No.: US 9,309,303 B2
(45) Date of Patent: Apr. 12, 2016

(54) COMPLEXATION OF FATTY ACID-CONJUGATED MOLECULES WITH ALBUMIN

(71) Applicant: The University of the Sciences in Philadelphia, Philadelphia, PA (US)

(72) Inventors: Zhlyu Li, Woodstock, MD (US); Russell Digate, Wilmington, DE (US)

(73) Assignee: The University of the Sciences in Philadelphia, Philadelphia, PA (US)

( * ) Notice: Subject to any disclaimer, the term of this patent is extended or adjusted under 35 U.S.C. 154(b) by 302 days.

(21) Appl. No.: 14/095,259

(22) Filed: Dec. 3, 2013

(65) Prior Publication Data

US 2014/0286863 A1    Sep. 25, 2014

Related U.S. Application Data

(62) Division of application No. 12/743,371, filed as application No. PCT/US2008/012943 on Nov. 20, 2008, now Pat. No. 8,598,311.

(60) Provisional application No. 61/004,056, filed on Nov. 21, 2007.

(51) Int. Cl.

| | |
|---|---|
| *C07K 14/00* | (2006.01) |
| *A61K 38/00* | (2006.01) |
| *C07K 14/765* | (2006.01) |
| *C07K 14/78* | (2006.01) |
| *A61K 49/00* | (2006.01) |
| *A61K 51/08* | (2006.01) |

(52) U.S. Cl.
CPC ............... *C07K 14/765* (2013.01); *A61K 49/00* (2013.01); *A61K 51/088* (2013.01); *C07K 14/78* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 5,879,907 | A | 3/1999 | Aberg et al. |
| 7,875,700 | B2 | 1/2011 | Radhakrishnan et al. |
| 2003/0118598 | A1 | 6/2003 | Hunt |
| 2005/0238664 | A1 | 10/2005 | Hunt |

FOREIGN PATENT DOCUMENTS

WO    WO-2008/088422 A2    7/2008

OTHER PUBLICATIONS

Moon et al., "Anti-angiogenic activity of conjugated linoleic acid on basic fibroblast growth factor-induced angiogenesis," *Oncol. Rep.*, May-Jun. 2003, 10(3):617-621 (Abstract only).

Raines et al., "Replacing a surface loop endows ribonuclease A with angiogenic activity," *J. Biol. Chem.*, Jul. 21, 1995, 270(29):17180-17184.

International Search Report and Written Opinion dated Sep. 28, 2009, from International Patent Application No. PCT/US2008/012943, 11 total pages.

International Preliminary Report on Patentability dated May 25, 2010, from International Patent Application No. PCT/US2008/012943, 6 pages.

*Primary Examiner* — Anand Desai

(74) *Attorney, Agent, or Firm* — Duane Morris LLP

(57) ABSTRACT

The present disclosure relates generally to novel methods and compositions for using engineered reprogramming factor(s) for the creation of induced pluripotent stem cells (iPSCs) through a kinetically controlled process. Specifically, this disclosure relates to establishing combinations of reprogramming factors, including fusions between conventional reprogramming factors with transactivation domains, optimized for reprogramming various types of cells. More specifically, the exemplary methods disclosed herein can be used for creating induced pluripotent stem cells from various mammalian cell types, including human fibroblasts. Exemplary methods of feeder-free derivation of human induced pluripotent stem cells using synthetic messenger RNA are also disclosed.

26 Claims, 23 Drawing Sheets

```
 -24  MKWVTFISLL FLFSSAYSRG VFRRDAHKSE VAHRFKDLGE ENFKALVLIA FAQYLQQCPF   36
  37  EDHVKLVNEV TEFAKTCVAD ESAENCDKSL HTLFGDKLCT VATLRETYGE MADCCAKQEP   96
  97  ERNECFLQHK DDNPNLPRLV RPEVDVMCTA FHDNEETFLK KYLYEIARRH PYFYAPELLF  156
 157  FAKRYKAAFT ECCQAADKAA CLLPKLDELR DEGKASSAKQ RLKCASLQKF GERAFKAWAV  216
 217  ARLSQRFPKA EFAEVSKLVT DLTKVHTECC HGDLLECADD RADLAKYICE NQDSISSKLK  276
 277  ECCEKPLLEK SHCIAEVEND EMPADLPSLA ADFVESKDVC KNYAEAKDVF LGMFLYEYAR  336
 337  RHPDYSVVLL LRLAKTYETT LEKCCAAADP HECYAKVFDE FKPLVEEPQN LIKQNCELFE  396
 397  QLGEYKFQNA LLVRYTKKVP QVSTPTLVEV SRNLGKVGSK CCKHPEAKRM PCAEDYLSVV  456
 457  LNQLCVLHEK TPVSDRVTKC CTESLVNRRP CFSALEVDET YVPKEFNAET FTFHADICTL  516
 517  SEKERQIKKQ TALVELVKHK PKATKEQLKA VMDDFAAFVE KCCKADDKET CFAEEGKKLV  576
 577  AASQAALGL                                                         585
```

Fig. 1

Domain I

Domain II

Domain III

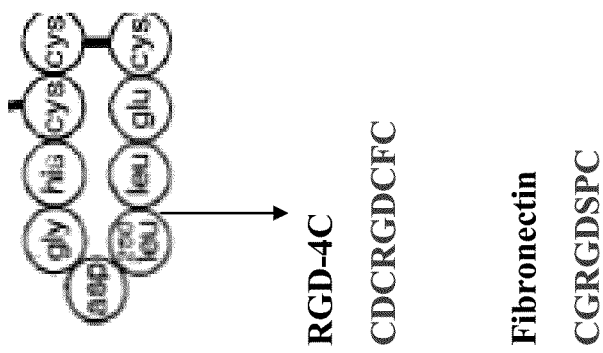
Fig. 3E

5'CGTAA CCGCGG TCA TAA GCC TAA GGC AGC TTG ACT3'
　　　　‾‾‾‾‾‾ ‾‾‾
　　　　Sac II  Stop

Fig. 7A

5'CGTAA CCGCGG C TAA GCC TAA GGC AGC TTG ACT3'
　　　　‾‾‾‾‾‾
　　　　Sac II

Fig. 7B

5'CGTAA CCGCGG TCA ACTAGT TAA GCC TAA GGC AGC TTG ACT3'
　　　　‾‾‾‾‾‾ ‾‾‾ ‾‾‾‾‾‾
　　　　Sac II  Stop  Spe I

Fig. 7C

5' CGTAA CCGCGG GCATGC GCTAGC AAGCTT TGCGCA TGT TTT TGC AAA TTC AGT TAC 3'
          Sac II    Sph I    Nhel    Hind III   Fsp I

Fig. 8A

5' CCTAT GCATGC GAC AA A TCA CTT CAT ACC CTT 3'
         Sph I

Fig. 8B

5' CCTAT AAGCTT TGC ACA GTT GCA ACT CTT CGT 3'
         Hind III

Fig. 8C

5' CGTAA CCGCGG GCATGC GCTAGC AAGCTT TGCGCA TAA TTT GTC TCC AAA AAG GGT ATG 3'
       ───── ────── ────── ────── ────── ──────
       Sac II  Sph I   NheI   Hind III  Fsp I

Fig. 9A

5' CCTAT GCATGC TGT GCA AAA CAA GAA CCT GAG 3'
         ──────
          Sph I

Fig. 9B

5' CCTAT GCTAGC  CAA GAA CCT GAG AGA AAT GAA TGC  3'
         ──────
          Nhe I

Fig. 9C

5' CGTAA CCGCGG GCATGC GCTAGC AAGCTT TGCGCA GCA GTC AGC CAT TTC ACC ATA 3'
         Sac II    Sph I    NheI   Hind III  Fsp I

Fig. 10A

5' CCTAT GCATGC TTC TTG CAA CAC AAA GAT GAC 3'
         Sph I

Fig. 10B

5' CCTAT AAGCTT CAA CAC AAA GAT GAC AAC CCC 3'
         Hind III

Fig. 10C

5' CGTAA CCGCGG GCATGC GCTAGC AAGCTT TGCGCA ACA TTC TGT AAA AGC AGC TTT 3'
       ‾‾‾‾‾‾ ‾‾‾‾‾‾ ‾‾‾‾‾ ‾‾‾‾‾‾ ‾‾‾‾‾
       Sac II  Sph I  NheI  Hind III  Fsp I

Fig. 11A

5' CCTAT GCATGC CTG TTG CCA AAG CTC GAT GAA 3'
         ‾‾‾‾‾‾
         Sph I

Fig. 11B

5' CCTAT GCTAGC CAA GAA CCT GAG AGA AAT GAA TGC 3'
         ‾‾‾‾‾‾
         Hind III

Fig. 11C

5' CGTAA CCGGCGG GCATGC GCTAGC AAGCTT TGCGCA GAT ATA CTT GGC AAG GTC CGC 3'
　　　　Sac II　　Sph I　　Nhe I　　Hind III　　Fsp I

Fig. 12A

5' CCTAT GCATGC TGT GAA AAA CCT CTG TTG GAA 3'
　　　　Sph I

Fig. 12B

5' CCTAT GCT AGC CAC TGC ATT GCC GAA GTG GAA 3'
　　　　Nhe I

Fig. 12C

5' CGTAA CCGCGG GCATGC GCTAGC AAGCTT TGCGCA GCA TTC CTT CAG TTT ACT GGA 3'
      Sac II   Sph I   Nhe I   Hind III  Fsp I

Fig. 13A

5' CCTAT GCATGC ATT GCC GAA GTG GAA AAT GAT 3'
        Sph I

Fig. 13B

5' CCTAT GCTAGC GTG GAA AAT GAT GAG ATG CCT 3'
         Nhe I

Fig. 13C

5' CGTAA CCGCGG GCATGC GCTAGC AAGCTT TGCGCA   GCA CTT CTC TAG AGT GGT TTC 3'
   ‾Sac II‾ ‾Sph I‾ ‾Nhe I‾ ‾Hind III‾ ‾Fsp I‾

Fig. 14A

5' CCTAT GCATGC   TAT GCC AAA GTG TTC GAT GAA TTT AAA 3'
         ‾Sph I‾

Fig. 14B

5' CCTAT GCT AGC   GTG TTC GAT GAA TTT AAA CCT 3'
         ‾Nhe I‾

Fig. 14C

5' CGTAA CCGCGG GCATGC GCTAGC AAGCTT TGCGCA ACA TTT GCT GCC CAC TTT TCC 3'
        Sac II   Sph I   Nhe I   Hind III  Fsp I

Fig. 15A

5' CCTAT GCATGC GCA GAA GAC TAT CTA TCC GTG 3'
         Sph I

Fig. 15B

5' CCTAT GCTAGC GTG GTC CTG AA CAG TTA TGT 3'
         Nhe I

Fig. 15C

5' CGTAA CCGCGG GCATGC GCTAGC AAGCTT TGCGCA   TAA CTG GTT CAG GAC CAC GGA 3'
   ‾‾‾‾‾‾ ‾‾‾‾‾‾ ‾‾‾‾‾‾ ‾‾‾‾‾‾ ‾‾‾‾‾‾
   Sac II  Sph I   NheI   Hind III Fsp I

Fig. 16A

5' CCTAT GCATGC  TGC ACA GAA TCC TTG GTG AAC 3'
         ‾‾‾‾‾‾
          Sph I

Fig. 16B

5' CCTAT AAGCTT G GTG AAC AGG CGA CCA TGC TTT 3'
         ‾‾‾‾‾‾
         Hind III

Fig. 16C

5' CGTAA CCGCGG GCATGC GCTAGC AAGCTT TGCGCA GCA CTT CTC TAC AAA AGC TGC 3'
      ‾‾‾‾‾‾ ‾‾‾‾‾‾ ‾‾‾‾‾‾ ‾‾‾‾‾‾ ‾‾‾‾‾‾
       Sac II  Sph I   Nhe I  Hind III  Fsp I

Fig. 17A

5'            CTTTGCCGAGGAGGGTAAAAAGCTTGTTGCTGCAAGTCAAGCTGCCTTAGGCTTATAGCCGC 3'
3' GTACGAAACGGCTCCTCCCATTTTTCGAACAACGACGTTCAGTTCGACGGAATCCGAATATCGG 5'

Sph I complementary          Hind III (K574L575)                    Stop
sticky end (A566C567)                                                Sac II
                                                                     complementary
                                                                     sticky end

Fig. 17B

COMPLEXATION OF FATTY ACID-CONJUGATED MOLECULES WITH ALBUMIN

RELATED APPLICATION DATA

This application is a Divisional application of U.S. application Ser. No. 12/743,371, filed May 18, 2010, now U.S. Pat. No. 8,598,311(B3497-00125); which claims priority to U.S. National Phase Application of International Application No. PCT/US2008/012943, filed Nov. 20, 2008 (B3497-00118); which claims priority to U.S. Provisional Application Ser. No. 61/004,056, filed Nov. 21, 2007 (B3497-00100).

BACKGROUND

The invention relates generally to the field of delivery of drugs, vectors, and other molecules in a variety of settings, including therapeutic, diagnostic, research and clinical uses.

Small organic molecules (i.e., those having molecular weights <10,000, and frequently <5,000 or <1,000) have well known uses as drugs in a variety of human ailments. Peptide and oligonucleotide drugs (including, for example, antisense oligonucleotides, ribozymes, aptamers, and siRNA/shRNA molecules) have emerged as powerful tools for drug target validation and promising therapeutics for a wide variety of human diseases. However, realization of the promise these agents offer as drugs has been hindered by the lack of efficient methods of delivering them to physiological sites at which they may exert useful activity. Obstacles to efficient delivery include considerations of in vivo stability, tissue and cell specificity, intracellular durability, immunogenicity, and toxicity of the agents. Many well-characterized small chemical drugs confront the same delivery bottlenecks that limit their potency in human applications.

Similarly, inorganic drugs (e.g., radioisotopes and radioisotope-containing compounds), imaging agents, and other small molecules intended for delivery to cells exhibit many of the same drawbacks with regard to their stability and delivery to desired cells and tissues.

Human Serum Albumin

Human serum albumin (HSA) is the most abundant protein in human plasma. HSA is known to bind an extraordinarily wide range of metabolites and drugs. Binding between HSA and such compounds affects, sometimes dramatically, their pharmacokinetics and pharmacodynamics.

HSA is synthesized in the liver and secreted as a non-glycosylated protein. It accounts for 60% of the mass of the plasma proteins and is present in the blood at a concentration around 0.6 mM with an average half-life of 14 days. Although the critical function of HSA in maintaining normal colloid osmotic pressure in plasma and in interstitial fluid is recognized, the molecular mechanisms of its basic physiological functions, such as metabolite transportation, exogenous chemical binding, and antioxidant protection, are not fully understood.

HSA is synthesized as a 585-residue single chain globular protein lacking prosthetic groups and glycosylation. The primary amino acid sequence of HSA is shown in FIG. 1. HSA has three homologous domains (designated domains I, II and III, as indicated in FIG. 2) that fold into the shape of a heart and each domain is classified into two subdomains (A and B). Further details of the structure of domains I, II, and III are shown in FIG. 3. Alpha-helixes account for approximately 67% of the secondary structure of HSA, and no beta-sheet secondary structure occurs in HSA. A unique feature of HSA is its 35 cysteine residues, 34 of which form 17 disulfide bonds. The only free cysteine (Cys-34, i.e., the cysteine residue that occurs at residue 34 of HSA) contributes significantly to the antioxidant activity of HSA and this residue can be chemical modified in a variety of known ways. The disulfide bonds are also responsible for the thermal stability of HSA. Others have recognized that the primary polypeptide structure of HSA includes several loops that are tightly held by disulfide bonds and present on the external surface of the protein.

Almost every body fluid contains some amount of HSA. In addition, HSA occurs within cells like ovarian cells, brain cells, peripheral nerve cells, lymphocytes, macrophages, and other cells. Tumor cells often take up HSA to a greater extent than non-tumorous cells of the same type. For example, albumin makes up 19% of the soluble protein of breast cancer cells.

Due to its availability, biocompatibility, nontoxicity, and immunogenicity, human serum albumin (HAS) has been used as a stabilizer in biopharmaceutical products (vaccine and recombinant protein), an adjuvant in drug formulation and a component of imaging agents. It also can be used to coat biomaterial surface and purify chiral chemicals. Moreover, adding signal peptides or functional compounds to albumin by chemical modification has been commonly used for drug targeting and delivery research. Using chemical crosslinking, HSA can also be formulated into microspheres and nanoparticles to encapsulate drugs, oligonucleotides, and radioisotopes for delivery or diagnosis purpose. However problems associated with the chemical modification may severely hinder the clinical application of chemically modified albumins. First, the modification is non-specific and non-homogenous. Second, these modifications change the physicochemical and biochemical properties of albumins and may result in an immune response. Third, the chemically modified albumin may not fold properly and exhibit an abnormal surface charge distribution. These changes are likely to be recognized by endogenous albumin and other serum proteins and cause aggregation and rapid elimination in vivo.

Long Chain Fatty Acids

Long chain fatty acids (LCFAs, i.e., carboxylic acids having an non-branched aliphatic chain having 16-20 carbon atoms in its backbone) are essential for many cellular functions. LCFAs serve as an important energy resource and are also critical components of lipids, hormones, and proteins. LCFAs are known to be bound and transported by HSAs within the human body.

Formation of conjugates between LCFAs and many small molecules is known to enhance the serum stability and delivery of the small molecules by a mechanism facilitated by binding of the small molecule-LCFA conjugate with HSA.

Shortcomings in stability, solubility, and 'targetability' limit the utility of many potentially useful drugs, diagnostic agents, nucleic acid vectors, and other relatively small molecules within the human body. The technology disclosed herein overcomes these shortcomings

BRIEF SUMMARY OF THE INVENTION

The disclosure relates to recombinant animal albumin proteins, such as human serum albumin (HSA). The recombinant proteins are fusion proteins having a ligand-binding protein domain inserted in place of a surface loop of the native (i.e., naturally-occurring form of the) protein. The ligand bound by the domain can be any of a wide variety of ligands including, for example, ligands that occur on the surface of a cell of an animal, ligands that occur in a tissue of an animal Examples of such domains include RGD-containing domains, adrenomedulin domains, endothelin-1 domains, matrix metalloproteinase 9 binding peptide domains, matrix metalloproteinase 2 binding peptide domains, and aminopeptidase N binding peptide domains.

The surface domains of animal albumin proteins are known. For example the surface loops of HSA have the amino acid sequences disclosed herein as SEQ ID NOs: 3-11. With reference to the naturally-occurring amino acid sequence of HSA (e.g., as shown in FIG. 1), the surface loops of HSA include (i) the loop defined by residues 53-62; (ii) the loop defined by residues 75-91; (iii) the loop defined by residues 91-101; (iv) the loop defined by residues 168-177; (v) the loop defined by residues 245-253; (vi) the loop defined by residues 265-279; (vii) the loop defined by residues 278-289; (viii) the loop defined by residues 360-369; (ix) the loop defined by residues 437-448; (x) the loop defined by residues 461-477; (xi) the loop defined by residues 476-487; and (xii) the loop defined by residues 558-567 of SEQ ID NO: 1.

The recombinant albumins described herein can be in the form of a complex that includes the albumin complexed with a compound that binds non-covalently therewith. The compound can be a conjugate of first molecule and a fatty acid. Examples of suitable first molecules include polynucleotides, polypeptides, and drugs other than polynucleotides or polypeptides. Other suitable examples of first molecules include radiolabeled compounds and imaging agents other than radiolabeled compounds. The fatty acid can be a $C_{10}$-$C_{20}$ fatty acid or, preferably, a $C_{16}$-$C_{20}$ fatty acid.

Another aspect of this disclosure pertains to a method of targeting a first molecule to a ligand. This method involves contacting a first composition and a second composition. The first composition includes a conjugate of the first molecule and a fatty acid. The second composition includes a recombinant animal albumin, as described herein. The first and second compositions are contacted for a time and under conditions sufficient for the conjugate to bind with the albumin to form a complex. After contacting the first and second compositions, the complex and the ligand are contacted. The ligand-binding domain of the albumin binds with the ligand and targets the first molecule to the ligand.

Another aspect of the technology described herein relates to a method of delivering a first molecule to a target within the body of a human. This method involves contacting a first composition and a second composition outside the body of the human. The first composition includes a conjugate of the first molecule and a fatty acid. The second composition includes a human serum albumin (i.e., naturally occurring HSA or a recombinant HSA of the type described herein). The first and second compositions are contacted for a time and under conditions sufficient for the conjugate to bind with the albumin to form a complex. Thereafter, the complex is administered to a tissue from which the target is accessible, and the first molecule is thereby delivered to the target. Suitable targets include cells and tissues of the human, and viruses, bacteria, parasites within the human. A preparation that includes the complex can be applied directly to a tissue wherein the target is located (or directly to a tissue that is itself the target). Alternatively, the preparation can be applied to an endothelial tissue that separates the target from the site of application. As another alternative, the preparation can be administered systemically (e.g., intravenously).

The albumin used in these methods can be normal human serum albumin, which can optionally be substantially purified, defatted, or both, prior to use in the methods. In one embodiment, substantially all first molecules not bound with the albumin after contacting the first and second compositions are removed from the preparation containing the complex prior to administering the preparation to the target. Furthermore, more than one conjugate can be bound with the albumin.

In another aspect, this disclosure relates to a method of enhancing delivery of a first molecule to a cell of a human prior to administering the first molecule to the human. The method involves conjugating the first molecule and a fatty acid to form a conjugate. A first composition that includes the conjugate and a second composition are contacted outside the body of the human. The second composition comprises a human serum albumin (native HSA or a recombinant HSA as described herein). The first and second compositions are contacted for a time and under conditions sufficient for the conjugate to bind with the albumin to form a complex. In the form of the complex, the first molecule exhibits enhanced delivery to human cells.

This disclosure further relates to compositions for delivering a first molecule to a cell of a human. The composition includes a human serum albumin (a native HSA or a recombinant HSA of the type described herein) having bound thereto a conjugate. The conjugate includes a fatty acid moiety conjugated with the first molecule. In this form, the first molecule can be delivered to a cell of a human. Preferably, the composition contains substantially no first molecules not bound with the albumin. In one embodiment, the albumin also has bound thereto a second conjugate. The second conjugate includes a second fatty acid moiety conjugated with a compound that binds specifically with a target molecule that occurs on the surface of the cell. In another embodiment, the second conjugate includes a second fatty acid moiety conjugated with a compound that binds specifically with a target molecule that occurs in a tissue that includes the cell.

BRIEF SUMMARY OF THE SEVERAL VIEWS OF THE DRAWINGS

FIG. 1 is a listing of the primary amino acid sequence (SEQ ID NO: 1) of human serum albumin (HSA). Residues 1 to 18 of SEQ ID NO: 1 are a signal peptide sequence, and residues 19 to 24 are a portion of the HSA propeptide that is cleaved from the mature protein, which has the amino acid sequence of residues 25 to 609 of SEQ ID NO: 1.

FIG. 3A shows the sequence (SEQ ID NO: 2) and loop structure of residues 53-62 of HSA. The disulfide linkage between the side chains of cysteine residues 53 and 62 is shown as a solid bar, and residues 1-52 and 62+ are not all individually listed. Shown in FIG. 3D are the sequences of RDC-4C (a RGD motif held by two pairs of disulfide bonds; SEQ ID NO: 3) of and an RGD-motif-containing portion (SEQ ID NO: 4) of fibronectin, either of which can be inserted in place of residues 53-62 of HSA. FIG. 3E is a ribbon model of the three-dimensional structure of the rHSA, in which disulfide bonds in the HSA structure are shown in red and residues 53-62 of HSA are shown in dark blue. The figure also shows the sequence (SEQ ID NO: 2) and loop structure of residues 53-62 of HSA and the RGD-4C sequence (SEQ ID NO: 3) and RGD-motif-containing portion of fibronectin (SEQ ID NO: 4).

FIG. 6 consists of FIGS. 6A and 6B.

FIG. 7 shows the sequences (SEQ ID NO: 14 in FIG. 7A; SEQ ID NO: 15: in FIG. 7B, and SEQ ID NO: 16 in FIG. 7C) of FRII3' primers described herein.

FIG. 8 shows the sequences (SEQ ID NO: 17 in FIG. 8A; SEQ ID NO: 18 in FIG. 8B, and SEQ ID NO: 19 in FIG. 8C) of FRI3' and FRII 5' primers described herein.

FIG. 9 shows the sequences (SEQ ID NO: 22 in FIG. 9A; SEQ ID NO: 23 in FIG. 9B, and SEQ ID NO: 24 in FIG. 9C) of FRI3' and FRII 5' primers described herein.

FIG. 10 shows the sequences (SEQ ID NO: 25 in FIG. 10A; SEQ ID NO: 26 in FIG. 10B, and SEQ ID NO: 27 in FIG. 10C) of FRI3' and FRII 5' primers described herein.

FIG. 11 shows the sequences (SEQ ID NO: 34 in FIG. 11A; SEQ ID NO: 35 in FIG. 11B, and SEQ ID NO: 36 in FIG. 11C) of FRI3' and FRII 5' primers described herein.

FIG. 12 shows the sequences (SEQ ID NO: 37 in FIG. 12A; SEQ ID NO: 38 in FIG. 12B, and SEQ ID NO: 39 in FIG. 12C) of FRI3' and FRII 5' primers described herein.

FIG. 13 shows the sequences (SEQ ID NO: 40 in FIG. 13A; SEQ ID NO: 41 in FIG. 13B, and SEQ ID NO: 42 in FIG. 13C) of FRI3' and FRII 5' primers described herein.

FIG. 14 shows the sequences (SEQ ID NO: 43 in FIG. 14A; SEQ ID NO: 44 in FIG. 14B, and SEQ ID NO: 45 in FIG. 14C) of FRI3' and FRII 5' primers described herein.

FIG. 15 shows the sequences (SEQ ID NO: 46 in FIG. 15A; SEQ ID NO: 47 in FIG. 15B, and SEQ ID NO: 48 in FIG. 15C) of FRI3' and FRII 5' primers described herein.

FIG. 16 shows the sequences (SEQ ID NO: 49 in FIG. 16A; SEQ ID NO: 50 in FIG. 16B, and SEQ ID NO: 51 in FIG. 16C) of FRI3' and FRII 5' primers described herein.

FIG. 17 shows the sequences (SEQ ID NO: 54 in FIG. 17A; SEQ ID NO: 55 in FIG. 17B) of an FRI3' primer and an HSA II fragment described herein.

DETAILED DESCRIPTION

Figure 2:
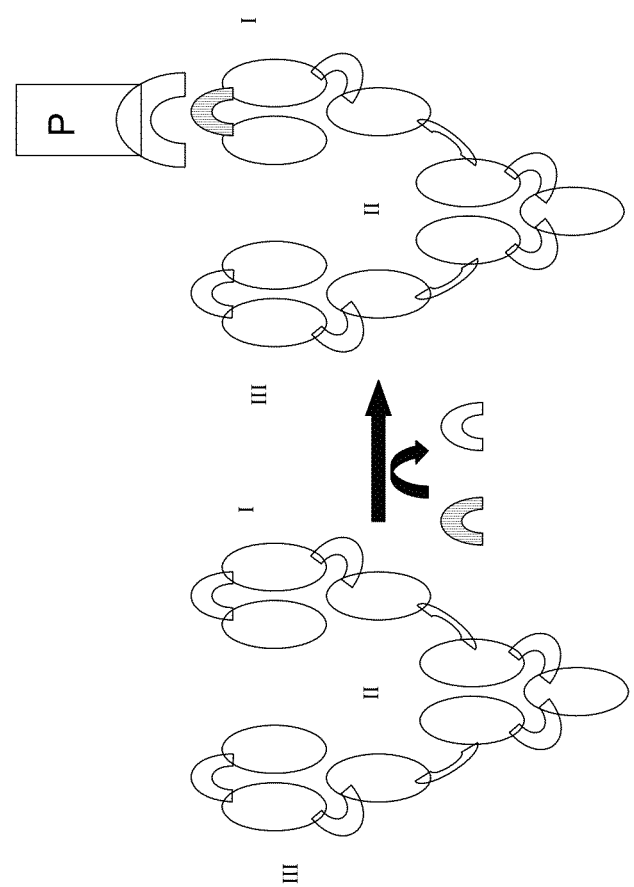
FIG. 2 is a diagram depicting the domain structure of HSA and replacement of a surface loop of HSA with an exogenous peptide sequence. In the diagram, the three lobular domains I, II, and III of HSA are depicted as aggregations of three sub-domains (open ovals). Peptide loops (open arcs) of HSA connect the sub-domains to one another and are located at or near the external (i.e., solvent-exposed) surface of the protein. In the diagram, an exogenous peptide domain (hatched arc) is substituted in place of one of the surface loops in domain I. The exogenous peptide domain has a ligand-binding domain that binds specifically with a particular ligand, shown in this diagram as a protein (P).

The technology disclosed herein relates to compositions and methods in which a fatty acid-conjugated compound is complexed with a human serum albumin (HSA) protein.

The complexes can be put to a wide variety of uses, depending on the components from which the complex is formed. For example, the complexes described herein are useful for improving delivery of drugs, imaging agents, and other molecules to cells of a human. The complexes are also useful as reagents for detection of various targets in biological and laboratory systems. Because moieties that exhibit highly specific binding affinities can be incorporated into the HSA, the complexes can be used as an alternative to antibodies for a wide variety of purposes for which antibodies are used. Albumin proteins modified to have such a moiety incorporated in place of a surface loop thereof are referred to herein as "target-binding albumins." Target-binding albumins can be used alone, or complexed with a fatty acid or a fatty acid-conjugated compound as a substitute for an antibody that exhibits a similar target-binding specificity.

The technology makes use of the native biochemical and physiological characteristic of human serum albumin (HSA) and fatty acids. The processes of conjugating molecules with fatty acids and of formulating HSAs having fatty acid-conjugated molecules bound thereto is simple, and the resulting compositions are simple and easy to manufacture. This disclosure is made in the context of HSA, which is suitable for in vivo use in humans. The technology can also be employed in substantially the same way to make complexes using fatty acid-conjugated albumins of other animals for in vivo use in those animals. For in vitro uses (i.e., in which introduction of the complexes into the body of an animal is not contemplated), the identity of the albumin used is not critical—substantially any albumin, as modified herein, can be used in such circumstances.

Advantage can be taken of ability of HSA to bind and transport native long chain fatty acids (LCFAs) and, significantly, molecules conjugated with LCFAs. Functional and therapeutic molecules can be delivered to body tissues in the form of fatty acid-conjugates, the conjugate being bound in a complex with HSA or in complex with a recombinant HSA (rHSA), as described herein. This approach differs from simply using fatty acid-conjugated molecules, which has been described by others. Fatty acid-conjugated polypeptides have been reported, for example.

As described herein, instead of directly administrating the conjugate to a human or other subject in vivo, the conjugate is first formulated with HSA in vitro under conditions that can be selected to favor (or optimize) formation of a complex between the conjugate and the HSA. The complex is thereafter delivered to a subject in vivo, either systemically or locally, or used in an in vitro application (e.g., in vitro delivery of a polypeptide or oligonucleotide to a cell). Non-complexed conjugate can be reduced or eliminated (e.g., by purification such as chromatography) in the preparation prior to its use. Complexation reduces or substantially eliminates binding of the conjugate with serum proteins of the subject in in vivo applications, and can reduce or eliminate undesirable binding of the conjugate with other components of an in vitro system. The complexation also reduces or eliminates enzyme degradation, renal excretion, and other undesirable fates that might befall the conjugate were it administered in a non-complexed form. The methods can also be used to reduce or prevent delivery of a conjugate to tissues in which the conjugate (or the de-conjugated molecule) has detrimental effects.

In in vivo applications, the conjugate-HSA complex described herein can be transported across endothelial cells by the process of transcytosis. The complexes made by the processes described herein can thereby reach the interstitial space of tissues in vivo, which represents an improvement in the ability of practitioners to target therapeutic and prophylactic agents to these body compartments. This property enables the complex to be administered to a patient by a wide variety of routes and in a wide variety of dosage forms. The complexes can be used to target a wide variety of tissues, such as solid tissues and blood cells, as well as other targets such as bacteria, viruses, and non-living materials. The complexes can be constructed, as described herein, to specifically bind with any of a wide variety of proteins, metabolites, or other molecules.

There are at least several benefits of the technology described herein. Probably chief among the benefits are the facts that HSA is biocompatible and its immunogenicity is limited. HSA-complexed, fatty acid-conjugated molecules share that biocompatibility and limited immunogenicity. On account of these properties, the methods described herein can be used to improve delivery and half-life and to reduce toxicity and side effects of pharmaceutical compounds (i.e., molecules which exhibit one or more therapeutic, diagnostic, and prophylactic effects on animal bodies) administered to animals. Such benefits can be achieved by conjugating the molecule with a fatty acid (preferably a $C_{16}$-$C_{20}$ LCFA) and complexing the resulting conjugate with an HSA (including an rHSA having an exogenous portion bearing a ligand-binding domain) prior to administering the compound to a subject. Such HSA-complexed, fatty acid-conjugated molecules can, instead of targeting delivery of a compound to a discrete body tissue, be used in vivo as complexes that bind particular cells or molecules that are believed or expected to be present in a biological system.

The technology described herein is a platform technology, and has a broad range of applications in drug formulation and delivery, radiotherapy, antibody-like targeting, proteomic analysis, biosensing, bioimaging, biomaterial processing, and other fields.

In vitro formulation of a complex of an HSA and a fatty acid-conjugated molecule has a number of advantageous features. For example, such formulation can greatly enhance serum solubility of the molecule, especially for lipophilic molecules. Such formulations also reduce random binding of the molecule (or the conjugate) with other serum proteins in vivo, and reduce elimination of the molecule (or conjugate) occasioned by binding with other serum proteins. Formulating a molecule in this way can prolong the time that the molecule remains in the circulation. Molecules formulated in this way can also be delivered more specifically to tissues or types of tissues than molecules not so formulated.

By way of example, HSA-complexed, fatty acid-conjugated molecules can be transported to tissues separated from the circulation by an interposed endothelial membrane by way of transendothelial transcytosis.

Further by way of example, fatty acid-conjugated molecules complexed with a rHSA which has an exogenous portion which binds specifically with a tissue target (e.g., a cell-surface protein) can be delivered specifically to cells or tissues that bear the target and that are accessible to HSA.

Still further by way of example, target-binding albumins described herein can be used to encapsulate drugs or other materials in order to take advantage of the binding specificity of the target-binding albumin Such compositions can optionally include a fatty acid-conjugated molecule (e.g., the encapsulated material or another compound) complexed with the target-binding albumin.

Because many cell types are able to take up HSA, the HSA-complexed, fatty acid-conjugated molecules described herein can be used to deliver the molecules to such cell types, even without adding an exogenous targeting domain to the HSA. This disclosure describes compositions and methods for formulating pharmaceutically active molecules (and other biocompatible molecules, such as imaging agents) that are versatile, in that any of a wide variety of molecules can be conjugated with any of a broad range of fatty acids, and in that the resulting conjugates can be complexed with naturally-occurring, synthetic, or recombinant HSA proteins. The rHSAs can include any of a wide variety of ligand-binding domains within their structure. The ligands that can be bound with such domains include substantially all of those that can be bound by a protein sequence insertable within the HSA surface domains described herein, and include small molecules, proteins, cells, extracellular matrix materials, metal ions, and others.

In addition to their uses as compositions to be administered directly to subjects, the composition described herein can be used to coat one or more surfaces of a biomaterial. Such coating improves the biocompatibility of the object (e.g., a drug nano- or micro-particle) of which the surface is a part. Such coatings can also be used to attract certain molecules or cells to the surface or to repel them from the surface. The coatings can be made by binding a fatty acid or fatty acid-conjugated molecule to a surface, and thereafter contacting the HSA (or rHSA) therewith. The coatings can also be made by binding the HSA (or rHSA) with the surface, and thereafter contacting the surface with a fatty acid or fatty acid-conjugated molecule. Similarly, the surface can be coated with a HSA (or rHSA) having a fatty acid or fatty acid-conjugated molecule already complexed therewith. If the rHSA is a target-binding albumin, then the material coated with the target-binding albumin can be used in a wide-variety of ways in place of materials coated with an antibody that binds the same target. Examples of such materials include those used for affinity separation and purification procedures, in vitro diagnostic tests, biosensing applications, and binding of a chromophore, a fluorophore, or another detectable marker with a target. In this last example, use of the target-binding albumins described herein can be preferable to use of a comparable antibody, in that the detectable marker need not be (although it can be) linked directly to the protein (i.e., the antibody or albumin), but can instead be conjugated with a fatty acid (or with a fatty-acid conjugated molecule) and complexed with the albumin, prior to, during, or after contacting the target and the albumin Definitions As used herein, each of the following terms has the meaning associated with it in this section.

"Human serum albumin" (HSA) refers to the protein generally known by the same name, having the structure described, for example, in Carter et al., (1989, Science 244 (4909):1195-1198, as described in entry no. NP_000468 of the NCBI's GenPept protein sequence database, and having the primary amino acid sequence (i.e., residues 25 to 609 of SEQ ID NO: 1) shown in FIG. 1.

"Peptide display" refers to a variety of known technologies whereby binding between a polypeptide expressed (i.e., "displayed") in an appropriate vector and a desired target can be screened and whereby information sufficient to reproduce the displayed polypeptide (e.g., a genetic sequence encoding the amino acid sequence of the polypeptide or an identifier correlatable with such a sequence) can be retrieved upon observation of binding (or non-binding). Peptide display technology is well known and includes, for example, phage display libraries wherein a multiplicity of virions each express on their surface a polypeptide and wherein binding between the expressed polypeptide and a target can be used to isolate and reproduce the virion expressing the polypeptide (whereby genetic material encoding the polypeptide can be obtained.) In the context of this disclosure, phage display technology for analyzing polypeptides displayed between disulfide-linked cysteine residues is of significant use.

A "recombinant" protein is a protein which has been engineered to have a primary amino acid sequence that differs from the naturally-occurring primary amino acid sequence of the protein. For example, a recombinant HSA (rHSA) has a sequence that differs from SEQ ID NO: 1, such as an rHSA having a fibronectin RGD-containing domain inserted in place of a surface loop of HSA, as described herein.

An "exogenous" portion of an amino acid sequence of a protein is a portion of the amino acid sequence that differs from the corresponding portion of the naturally-occurring sequence of the protein as a result of a change made or induced by man in the nucleic acid sequence that encodes the protein.

A polypeptide is inserted "in place of" a surface loop of an HSA if at least most (i.e., >50%, and preferably all) of the contiguous residues that normally occur between the disulfide-bound cysteine residues that define the surface loop are absent and replaced by the polypeptide.

Detailed Description

Uptake of long chain fatty acids (LCFAs) is an essential cellular metabolic process. It is known that cell are able to take up LCFAs by means of receptor-mediated binding and transmembrane transportation. LCFAs are also known to taken up by cells by means of passive diffusion. It is also known that cells can translocate LCFA across the cellular membrane by means of pathways mediated by albumin proteins that are capable of binding with LCFAs and translocating across cellular membranes.

The technique of fatty acid conjugation of peptides and other small molecules has been used by others to modify therapeutic peptides in order to prolong in vivo circulation. It is thought that the conjugate is taken up by substantially the same means as LCFAs and that prolongation of conjugate circulation may be related to complexation of the conjugate with albumins present in blood. However, in vitro conjugation of a molecule with a fatty acid, together with (still in vitro) complexation of that conjugate with a human serum albumin (HSA) protein has not been previously reported. This in vitro conjugation-and-complexation process is described herein.

The process described herein is simple to perform and can be used for a wide variety of molecules to be delivered to a subject. The process is performed in vitro, and significant control can therefore be exerted over the process, which control cannot be exerted in systems in which complexation of HSA and fatty acid moieties is left to the vagaries of biological systems such as the human blood stream and peritoneal cavity. This controlled, in vitro processing permits improved control of the pharmacodynamic and pharmacokinetic profiles of molecules (e.g., drugs) that are included in the complex.

Further described herein are methods of modifying the structure of HSA in order to cause it to bind specifically with a protein or other ligand that occurs within a subject's body. Molecules formulated with such recombinant HSAs (rHSAs) permit targeting of compounds to particular body locations, to particular types of cells, or to other structures that act as a ligands with a protein ligand-binding domain or motif. The technology described herein can serve as a platform technology for applications in drug formulation and delivery, radiotherapy, bioimaging, and biomaterial processing.

The technology described herein is directed to conjugating various therapeutic or functional molecules, such small chemical drugs, peptides, oligonucleotides, isotopes and imaging regents with fatty acids, such as LCFAs. The fatty acid-conjugated molecules are then bound to an HSA to form a complex in vitro. This approach differs from previous methods, wherein fatty acid-conjugated molecules were used to attempt to achieve improved delivery of the molecules. An aspect of this process, the criticality of which was not previously appreciated, is that formation of a complex between HSA and the LCFA-molecule complex should be completed ex vivo—i.e., outside the body of the human to which the complex is to be administered. For in vitro uses of the complex, the complex is also formed in vitro—i.e., outside the body of any animal from which the albumin may be obtained.

Described herein are methods of delivering a molecule to a cell within the body of a subject such as a human. The method includes the steps of contacting a first composition and a second composition outside the body of the subject. The first composition includes a conjugate of the molecule and a fatty acid. The second composition includes a human serum albumin protein. The two compositions are contacted for a time and under conditions sufficient for the conjugate to bind with the albumin to form a complex.

Compositions made in this way can be administered to a tissue, fluid, or body compartment from which is accessible the cell to which delivery of the molecule is desired. The fact that HSA is found in many human cell types indicates that the methods and compositions described herein can be used to deliver molecules to at least those cell types.

The HSA protein used in the compositions and methods described herein can be engineered to form rHSAs that include within their structure a functional polypeptide sequence, such as a polypeptide domain that binds specifically with a particular ligand or type of ligand. Such functional polypeptides can be incorporated in place of one of the surface loop portions of the naturally occurring HSA sequence, the surface loops being defined by the disulfide-linked cysteine residues of HSA that are identified elsewhere herein. It is immaterial whether the disulfide-linked cysteine residues that define the boundary of the replaced surface loop in the rHSAs described herein are derived from an unmodified HSA, derived from the functional polypeptide, or derived from both. The disulfide-linkage serves to isolate the secondary- and tertiary-structure-inducing effects of the functional polypeptide from the remainder of the rHSA, preserving both the functions and conformation of HSA and the function and conformation of the functional polypeptide.

The identity of the ligand and can be selected by the person engineering the rHSA. By way of example, suitable ligands include cellular membrane proteins, extracellular matrix proteins, protein markers associated with the cells, serum proteins and metabolites, body fluid proteins and components, virus proteins, and bacterial proteins.

More than one functional polypeptide sequence can be inserted within an rHSA. For example, an rHSA can have a polypeptide domain that binds specifically with a first ligand inserted in place of one of the surface loops of the corresponding HSA, a second polypeptide domain that binds with a second ligand in place of another of the surface loops of the HSA, and so on. More than one polypeptide domain that binds with the same ligand can be inserted within different surface loops of the HSA, even if the domains bind with the same portion of the ligand such that binding of one domain with a ligand molecule precludes or obscures binding of the second domain with the same ligand molecule. Clearly, domains that bind with different domains of a single ligand molecule can be used. Similarly, domains that bind specifically with entirely different ligand molecules can be used.

In the context of a rHSA protein engineered to include a polypeptide sequence that binds with a portion of target protein, it is immaterial whether the target protein or the corresponding target protein-binding sequence of the rHSA is referred to as the "ligand." The target protein can, for example, be a cell surface receptor protein that specifically binds with (i.e., has as a "ligand" of the receptor protein) a certain protein structure, and that structure can be incorporated into the rHSA surface loop domain. What is important is that the "ligand-binding domain" of the rHSA bind specifically with a structure present in the target (e.g., a structure present on a cell surface protein of a target cell type in a human's body). The structure to which that domain binds can be a protein, or it can be any other molecules known to bind specifically with protein domains, such as carbohydrate structures, extracellular matrix components, mineral substrates (e.g., bone matrix), viruses, or bacterial cells.

An important aspect of the compositions and methods described herein is that they can limit delivery of molecules to only selected (i.e., selectable) portions of the body of the human to whom they are administered. Many pharmaceutical agents, for example, exert beneficial effects at some body locations, but exert deleterious effects at other body locations. Similarly, it is desirable to use some agents (e.g., radionuclides and imaging agents) at the lowest dose that is practical, in order to minimize exposure of the human to the agent. The ability of the compositions described herein to direct delivery of such agents to particular locations, structures, or cell types where they are to act is beneficial.

The compositions and methods described herein have significant in vitro and in vivo uses stemming from the ability of the HSA and the fatty acid-complexed molecule to exhibit independent target-binding abilities. By way of example, a rHSA described herein can include a polypeptide portion inserted in place of a surface loop of HSA, wherein the portion confers the ability to bind to a first target to the rHSA. A molecule (e.g., a polypeptide, a polynucleotide, or a small molecule such as a carbohydrate) capable of binding a second target can be conjugated with a fatty acid, and the fatty acid-conjugated molecule can be complexed with the rHSA. Such pairs of rHSAs and fatty acid-conjugated molecules can be used to bind a second target in the vicinity of a first target, to bind a first target in the vicinity of a second target, or to separately bind first and second targets and subsequently (i.e., upon complexation) bring together the bound first and second targets. A skilled artisan recognizes that a wide variety of situations in which such functionalities can be used, including purification, targeting, probing, binding, coating, and detection uses.

Particular aspects of the compositions and methods described herein are described in greater detail below.

Conjugation of a Fatty Acid and a Molecule to be Complexed with a HSA

LCFAs (16-20 carbons) are essential for many cellular functions. Although the mechanisms of LCFA uptake by various cells are not fully understood, non-esterified fatty acids are bound and transported by albumins (the binding constant being from about 0.05 to 1 micromolar for myristic acids). HSA binding increases the effective aqueous solubility of hydrophobic LCFAs to the millimolar range in blood and serum. One HSA molecule is able to bind from about 0.1 to 2 molecules of LCFA under normal physiological conditions and carries up to 6 molecules of LCFA after exercise, fasting, adrenergic stimulation, and under certain pathological conditions. The crystal structures of complexes formed between LCFAs and HSA reveals at least 5 primary binding sites and 4 putative binding sites. LCFA-conjugated molecules bind to HSA and the pharmacokinetic profiles (and corresponding therapeutic capacity) of the molecules are altered thereby. In each actual and putative binding site in the HSA-LCFA complex, the carboxylate head-group of the LCFA is rigidly held in place by electrostatic interactions and hydrogen bonds, and the methylene tail is accommodated in a relative hydrophobic cavity of HSA.

Since the carboxylate head and the methylene end are located accessible to the protein surface, it was hypothesized that chemical modifications at these two ends would be tolerated without disrupting LCFA binding with HSA. For this reason, it is preferable to conjugate a molecule that one wishes to deliver to a human cell at or near (i.e., within a few molecular bonds of) one end or the other of a fatty acid, and preferably at or near an end of a LCFA. The interactions between HSA and the fatty acid serve to anchor the molecule to the HSA, by means of binding between HSA and the fatty acid. The identity of the fatty acid used in the compositions and methods described herein is not critical, because the ability of albumins such as HSA to bind with a variety of fatty acids is known. $C_{10}$-$C_{20}$ fatty acids (i.e., those which have from 10 to 20 carbon atoms in their chemical structure are suitable, and $C_{16}$-$C_{20}$ fatty acids may be particularly useful. The degree of branching and unsaturation are not critical, and straight chains fatty acids and those having limited unsaturation are recognized as being among the fatty acids common in the diet and naturally occurring in animals such as humans. Each of these fatty acids is suitable for use in the compositions and methods described herein.

The chemical means or bonds by which the molecule is conjugated with the fatty acid are not critical. In one embodiment, the conjugation of the molecule and fatty acid is selected on the basis of being reversible upon uptake of the conjugate within a cell (i.e., the conjugating linkage is physiologically reversible). By way of example, the reducing environment present in many cells can result in cleavage of a disulfide bond between a molecule and a thiol-substituted fatty acid, resulting in generation of free molecule and free fatty acid upon uptake of the conjugate into a cell. Physiological reversibility of the conjugation is not necessary unless the conjugation prevents the molecule from exhibiting its desired function. By contrast, conjugation that limits or eliminates a property of the molecule to be delivered can be beneficial for preventing inappropriate exhibition of that property prior to cellular uptake.

In one embodiment, the fatty acid can be conjugated with a portion of a peptide that can be cleaved by an enzyme known to occur at (or supplied to) a body location at which release of the fatty acid from the peptide is desired. When the complex described herein (or the fatty acid conjugate alone) encounters the enzyme, cleavage of the peptide occurs with release of the fatty acid from the cleaved portion of the peptide.

In another embodiment, the fatty acid can be conjugated with a peptide and selected to be a fatty acid moiety that is cleavable by a lipase enzyme, such as a phospholipase. When the complex encounters the lipase, cleavage of the fatty acid moiety from the peptide moiety occurs.

By way of example, a method of conjugating a polynucleotide (e.g., single- or double-stranded DNA or RNA) with a fatty acid are illustrated here. The oligonucleotide can be first modified at the 5'- or 3'-end using an amine carbon modifier, resulting in a molecule having the structure $NH_2$—$(CH_2)_n$-polynucleotide. Examples of amine carbon-modifying reagents are known in the art. These linkers can be added to the 5'-end, to the 3'-end, or to both ends of the polynucleotide. They can also be added to modified base residues within the polynucleotide by known methods. The amine-modified polynucleotide is conjugated with the carboxyl group of a fatty acid, forming an amide bond and resulting in a conjugate having the structure $CH_3$—$(CH_2)_m$—CONH—$(CH_2)_n$-polynucleotide, wherein m and n are independently integers. The length of the fatty acid can be selected, using routine methods, for optimal HSA binding for different forms and lengths of polynucleotide. Similarly, a fatty acid and a polypeptide can be conjugated by forming an amide bond using the fatty acid carboxyl group and an amine group (i.e., an N-terminal amine or a primary amine side group, such as that of lysine) to yield the structure $CH_3$—$(CH_2)_m$—CONH-polypeptide. Likewise, employing an analogous conjugation strategy, other relatively small molecules can be conjugated to the carboxyl end of fatty acids through amide bonds.

Further by way of example, a method of conjugating a polynucleotide (e.g., single-stranded DNA or RNA) with a fatty acid are illustrated here. The oligonucleotide can be first modified at the 5' or 3' end using a thiol carbon modifier (resulting in a molecule having the structure HS—$(CH_2)_n$-polynucleotide). Examples of thiol carbon-modifying reagents are known in the art. The thiol-modified oligonucleotide can be conjugated using the thiol group of 1-mercapto fatty acids (HS—$(CH_2)_m$—COOH) to form a disulfide bond, yielding a conjugate having the structure polynucleotide-$(CH_2)_n$—S—S—$(CH_2)_m$—COOH. As with amide-conjugated conjugates, the length of the fatty acid can be selected, using routine methods, for optimal HSA binding for different forms and lengths of polynucleotide. Similarly, a fatty acid and a polypeptide can be conjugated by forming a disulfide bond using a thiol group of a cysteine amino acid of the polypeptide and a 1-mercapto fatty acid, to yield the structure polypeptide-S—S—$(CH_2)_m$—COOH. Likewise, employing an analogous conjugation strategy, other relatively small molecules can be conjugated to the methylene end of the fatty acid by way of, for example, a disulfide bond.

Instead of, or in addition to, amine and thiol linkers, carboxyl linkers can also be used to conjugate fatty acids (or $C_{10}$-$C_{20}$ hydrocarbons) to a molecule such as a polynucleotide (e.g., forming a structure having a formula like COOH—$(CH_2)_n$-polynucleotide). In this embodiment, a carboxyl linking group is attached to the polynucleotide using known methods. A primary amine having a $C_{10}$-$C_{20}$ hydrocarbon tail (i.e., a compound having a structure like $CH_3$—$(CH_2)_m$—$NH_2$) can thereafter be conjugated with the carboxyl moiety, yielding a primary amine moiety linked to the polynucleotide and having a fatty acid-like hydrocarbon tail (i.e., a compound having a structure like $CH_3$—$(CH_2)_m$—NHCO—$(CH_2)_n$-polynucleotide).

For example, a peptide can be conjugated with a fatty acid by way of a carboxyl, amine, or sulfhydryl group. Further by way of example, a carbohydrate can be conjugated with a fatty acid by way of a hydroxyl group of the carbohydrate. Similarly, any molecule (including, for example, a small pharmaceutically-active agent) can be conjugated with a fatty acid by way of any of these, or other known reactive centers, using methods known in the art.

When conjugating molecules with a fatty acid, it is not critical that all of the molecules or all of the fatty acids are conjugated following the conjugation reaction(s). However, if it undesirable to include non-complexed, non-conjugated molecule in the composition to be administered to a human, then it can be desirable to remove non-conjugated molecule, non-conjugated fatty acid, or both, following the conjugation reaction and prior to complexing the conjugate with the HSA. Alternatively, non-conjugated molecule can be separated from HSA-complexed, fatty acid-conjugated molecule after the products of the conjugation reaction(s) are complexed with the HSA. Because the fatty acid use must be able to form a complex with the HSA, it may be impractical to remove non-conjugated fatty acid from the composition after contacting the products of the conjugation reaction(s) are complexed with the HSA. For that reason, if complexation on non-conjugated fatty acid is undesirable, then non-conjugated fatty acids should be separated from the products of the conjugation reaction(s) prior to contacting those products with the HSA, for example by reverse phase chromatography.

The identity of the molecule that is complexed with the fatty acid is not critical. A wide variety of molecules can be conjugated with a fatty acid and the resulting conjugate can be complexed with a HSA. For molecules intended to be delivered by way of a body fluid such as blood or peritoneal fluid, the molecule should be selected such that the complex formed after conjugating the molecule with the fatty acid and complexation of that conjugate with the HSA exhibits at least minimal solubility in the body fluid (in many instances, it is immaterial whether the complex is dissolved or suspended in the fluid). Similarly, appropriate physical forms (e.g., suspensions and solutions) of the complex are apparent to the skilled artisan for administration, depending on the identity of the route of intended administration and the corresponding body fluid our surface. The methods described herein can be used even with completely (or nearly completely) insoluble molecules and materials. By way of example, a plastic material (various polymeric materials, including, e.g., the housing of an implantable device) can be conjugated with a fatty acid, and the conjugated material can be contacted with a HSA prior to implanting the device, to minimize immunogenicity and binding of proteins other than HSA with the material following implantation.

The identity of the molecule to be conjugated with a fatty acid and complexed with an albumin is not critical. Although it is foreseeable that there will be an upper limit on the size (e.g., as assessed by molecular weight or number of monomeric units) of the molecule that can be effectively conjugated and complexed, a skilled artisan understands that the upper limit, if any, can be determined empirically, and such determination involves no more than the exercise of normal experimental technique. By way of guidance, double-stranded oligonucleotides having a length of about 30 base pairs can be conjugated and complexed, and those having a length not greater than 22 base pairs appear to be particularly amenable to conjugation and complexation using the methods described herein. Similarly, polypeptides having a length of about 40 amino acid residues can be conjugated and complexed, and those having a length not greater than 20 residues appear to be particularly amenable to conjugation and complexation using the methods described herein. The relative hydrophobicity and hydrophilicity of the compound to be conjugated and complexed do not appear to be of particular importance.

It is not critical that the molecule be conjugated with one (i.e., and only one) species of fatty acid. The molecule can be conjugated with a mixture of fatty acids (e.g., a mixture of $C_{10}$-$C_{20}$ fatty acids) yielding conjugates in which the molecule-moiety is identical among the conjugates, but in which the fatty acid moieties vary among the conjugates. Likewise, if conjugation with substantially only a single fatty acid species is desired, it is not critical that the fatty acid be free of all other fatty acids. Either synthetic (i.e., non-biologically-synthesized) fatty acids or fatty acids obtained from a biological source can be used, it being recognized that fatty acids obtained from natural sources often contain a mixture of fatty acid species.

Details of reagents and reaction conditions not specifically described herein are readily determinable by a skilled artisan in this field.

Complexing HSA with the Fatty Acid-Conjugated Molecule

The target-binding albumins described herein can be used on their own, without a fatty acid-conjugated molecule complexed therewith. In important embodiments of the methods and compositions described herein, a fatty acid-conjugated molecule is present in a complex wherein at least the fatty acid portion of the conjugate interacts with an HSA protein described herein, such as an rHSA or one of the target-binding albumins described herein. This complex is formed by contacting the conjugate with a composition that includes HSA. The conjugate and the HSA-containing composition are contacted for a time and under conditions sufficient for the conjugate to bind with the albumin to form a complex.

The duration and conditions under which the compositions need be contacted depend on the particular properties of the molecule, the fatty acid, and the HSA that are used, and these duration and condition parameters are readily determinable by a skilled artisan in this field. By way of example, when the first molecule is a polypeptide having the sequence CHLDAHWKG (SEQ ID NO: 5) and is conjugated with the fatty acid derivative 16-methanethiolsulfonyl hexadecanoic acid by way of the thiol group of the cysteine residue of the polypeptide, and that conjugate is contacted with naturally-occurring HSA in a phosphate-buffered saline solution at 20 degrees Celsius, complexation of the conjugate and the HSA will normally be essentially complete within about 30 minutes. A skilled artisan in this field recognizes that the reagents and reaction times that are appropriate depend on the chemical characteristics of the fatty acid and molecule-to-be-conjugated species. If not predictable from the identity of the species, the skilled artisan understands that they can be determined empirically using no more than ordinary experimentation. The HSA with which the conjugate is to be complexed is preferably present in excess (e.g., 2- to 5-fold molar excess), and the precise ratio of conjugate to HSA is not critical. The time required for approximately equilibrium binding between the HSA and the conjugate is dependent on the chemical species involved, the temperature, the degree and type of agitation, and other factors readily known to the skilled artisan. The duration for which complex formation is allotted is not critical and should generally be on the time scale of minutes to hours (typically 30 minutes to 12 hours, with preference for durations less than several hours).

The HSA can be a naturally-occurring HSA or a synthetic HSA protein. Synthetic HSA proteins can have the same primary amino acid structure as naturally-occurring HSA, or they can be engineered to have a different amino acid structure (so long as normal HSA activities are substantially preserved; i.e., so long as the HSA exhibits the biochemical and biological properties of HSA). HSA and the recombinant HSAs described herein must be used in human in vivo applications. For in vivo applications in another animal, an albumin that occurs naturally in that other animal must be used, and non-human animal albumins can be complexed with fatty acid-conjugated molecules just as described herein for HSA. For in vitro application, the immune response of an animal against the albumin of a different animal need not be considered, and substantially any albumin can be used. Thus, while the compositions and methods described herein have been discussed primarily in the context of using HSA, substantially the same compositions and methods can be made and performed for in vitro uses using albumins obtained from other animals, such as bovine serum albumin.

HSA can obtained from a natural source (e.g., from blood or plasma harvested from a human donor). HSA can also be obtained from an organism (e.g., a bacterium, a fungus, a plant cell culture, or an insect cell culture) that does not normally produce HSA, but has been engineered to do so. A characteristic of HSA obtained from natural sources is that the HSA so obtained can bind with fatty acids that occur in the organism or the medium in which it is produced. HSA saturated with fatty acids or lipids can exhibit a limited capacity to form a complex with the fatty acid-molecule complexes described herein. If the HSA with which a complex is to be formed has been obtained from a natural source, then it can be desirable to remove some or all of the fatty acids and lipids that are associated with the HSA prior to contacting the HSA with the fatty acid-molecule conjugate described herein. Such a process is commonly referred to as "defatting" the HSA, and substantially any known defatting procedure can be used. An example of a suitable defatting procedure (one involving charcoal treatment) is described in Chen, 1967, J. Biol. Chem. 242:173-181.

A preparation of HSA obtained from a natural source can include as contaminants other molecules that naturally occur in the source. For example, HSA preparations obtained from an organism that produces the HSA can be contaminated with other proteins normally produced by the organism. Furthermore, if the HSA is obtained from a human, the HSA preparation can include as a contaminant one or more human pathogens. Thus, although human blood and other human body fluids can be convenient and economical sources of HSA, the risk of pathogenic contamination by the fluid donor can make HSA obtained from non-human sources (e.g., cultured plant or insect cells) a preferable reagent in the compositions and methods described herein.

The conditions under which and apparatus with which the composition including the HSA and the composition including the fatty acid-molecule conjugate are contacted are not critical. The goal of such contacting is to bring the conjugate into sufficient proximity to the HSA that the forces of molecular attraction between the HSA and the fatty acid portion of the conjugate are able to act and cause complex formation. If the HSA and the conjugate are both soluble in a solvent that does not significantly denature the HSA, then the HSA and the conjugate can simply be combined in the solvent, and stirring or other agitation need not be applied. If the conjugate is in a solvent that is substantially insoluble with the solvent in which the HSA is suspended, then an interface will exist between the two solvents, and complexation can occur substantially only at the interface. In such instances, procedures for contacting insoluble liquid phases (e.g., stirring, shaking, mixing, or emulsification) can be performed in order to increase the rate of complex formation. If such procedures are employed, care should be taken to avoid denaturing or otherwise damaging the HSA.

Considerations of appropriate liquid contacting procedures are well known in the art and a skilled artisan can select appropriate conditions without significant experimentation by taking into account the identity and nature of the solvents, the properties of the HSA and the conjugate, the temperature, the type and degree of agitation, and other factors within the ken of the skilled artisan.

An HSA protein can form a complex with multiple copies of the molecule-fatty acid conjugate. For example, if the HSA is not complexed with any other lipid or fatty acid, naturally-occurring HSA can form a complex with at least five conjugates. Several other putative fatty acid-binding sites are recognized in HSA, so it is possible that more than 5 (e.g., 10, 12, or 14) conjugates can be complexed with a single HSA molecule. With these guidelines in mind, the ratio of HSA molecules to conjugates that are contacted is not critical. It is not necessary that every fatty acid-binding site of the HSA be occupied with a conjugate molecule. It can be desirable to include as many conjugates in the complex as possible, and this can be achieved by contacting an excess (e.g., 20-fold molecular excess) of the conjugate with the HSA and permitting the complexation to proceed essentially to equilibrium. Appropriate HSA-to-conjugate ratios can be determined empirically as well.

Complexes containing more than one type of fatty acid-molecule conjugate can be formed by contacting the HSA with multiple types of conjugates. The contacting can be performed in multiple steps (e.g., contacting HSA with a first conjugate and thereafter with a second conjugate) or by contacting the HSA with a composition that includes multiple conjugates. The conjugates can be conjugates of a single fatty acid with different molecules. Alternatively, the same molecule can be conjugated with different fatty acids. The mixture of conjugates can include conjugates that vary both in their fatty acid moiety and their other-molecule moiety. Such mixed conjugates/complexes can be used, for example, as combination therapy whereby two drug moieties can be targeted to a single cell type, each drug affecting a different biochemical pathway or target in the cell. Such complexes can also include one conjugated-molecule that tends to favor targeting of selected cells by the complex, while another conjugated-molecule of the complex has a desired biological effect on the targeted cell. By way of example, a complex can include a fatty acid-conjugated ligand of a cell surface receptor expressed on a desired cell type for the purpose of targeting the complex to the desired cells, and the complex can further include a fatty acid-conjugated moiety (e.g., a polypeptide or an oligonucleotide) for the purpose of delivering the moiety to the desired cells.

In one embodiment, the HSA is contacted with a second conjugate in addition to the fatty acid-molecule conjugate. The second conjugate is a second fatty acid moiety (i.e., either the same fatty acid moiety as in the fatty acid-molecule conjugate or a different fatty acid moiety) conjugated with a compound that binds specifically with a target molecule that occurs on the surface of a cell to which the composition is to be targeted or a target molecule that occurs in a tissue to which the composition is to be targeted. In these embodiments, it is interaction between the second conjugate and the target that directs the complex (including the molecule to be delivered) to the target.

In another embodiment, the HSA is contacted with a second compound that forms a complex with HSA, but is not a fatty acid-conjugated molecule. Numerous compounds (including many drugs, especially those having significant hydrophobic portions) are known to form complexes with HSA when the compound is contacted with HSA. Such compounds can be complexed with an HSA described herein (e.g., a rHSA or a target-binding albumin), either in vitro or in vivo. The complex can also be contacted with a fatty acid-molecule conjugate of one of the types described herein, thereby forming a complex that includes the HSA, the compound, and the conjugate. Formation of the complex in vitro and separation therefrom of non-complexed components can yield complex having greater homogeneity and a more controlled composition than would be formed if the components were separately administered to an animal or to another system. In fields such as drug delivery, homogeneity (or at least partial control) of complex structure can be beneficial.

Complexation of the HSA with the conjugate preferably occurs after the conjugation reaction is complete or substantially complete. Although the complexation can be performed simultaneously with conjugation, performance of the two reactions simultaneously can result in conjugation of HSA with the fatty acid, with the molecule, with other HSA molecules, or with some combination of these.

Purification

The compositions described herein can be purified to remove undesirable components at various stages, using any of the wide variety of purification technologies known in the art. By way of example, it can be undesirable to have reagents employed in the fatty acid-molecule conjugation reaction present when the conjugate is complexed with HSA (i.e., because conjugation of the conjugate or other components to HSA is undesirable). It can be preferable, therefore, to purify the conjugate from such reagents. The term "purify" does not refer to purity in a philosophical sense (i.e., utter absence of the non-desired species), but instead means reduction of the concentration of non-desired molecules to levels at which the magnitude of their undesirable effects is acceptable. Acceptable degrees of purity are readily determinable by a skilled artisan in view of the disclosure provided herein.

Formation of the fatty acid-conjugated, HSA-complexed molecular species described herein can be desired in order to avoid an undesirable property or effect of the non-conjugated, non-complexed molecular species. As with substantially all chemical reactions, the conjugation and complexation reactions described herein cannot be expected to yield homogenous compositions which include the fatty acid-conjugated, HSA-complexed molecular species in the complete absence of non-conjugated and/or non-complexed species. If undesirable properties of those species are to be avoided upon administration of the composition to a human, it can be desirable to separate those non-conjugated and/or non-complexed species from the composition prior to administration. Any of the wide variety of purification procedures (e.g., chromatography, electrophoresis, centrifugation) known in the art can be used to effect such purification. A quick, simple, and effective way of separating relatively large molecules from substantially smaller molecules is ultrafiltration, in which pressure is applied to a liquid mixture above a membrane having pores of sufficient size to substantially retard passage of the large molecules while permitting passage of small molecules. Ultrafiltration methods can be used to purify products described herein from substantially smaller molecular species (e.g., from conjugation reagents or from non-conjugated, non-complexed drug molecules).

Recombinant HSA (rHSA) Proteins

Chemically-modified HSAs, monoclonal antibodies, ligand- or peptide-conjugated polymers, and liposomes have been applied by others to achieve drug targeting and delivery. However, availability, biocompatibility, toxicity, durability and immunogenicity have limited the clinical and other application of those approaches. By contrast, the technology described herein can be employed to form a complex of HSA with a fatty acid conjugate of such compounds, such complexes optionally including other components, as described herein.

In an important embodiment, the HSA that is used in the methods described herein can be a rHSA that exhibits a molecular or cellular targeting function. Design and production of recombinant proteins has become routine, and a skilled artisan in this field is able to construct a wide variety of rHSAs in view of the information described herein and the information available in the art. In contrast to prior descriptions, this disclosure emphasizes the importance of inserting a polypeptide sequence that confers a molecular or cellular targeting function in place of a disulfide-bounded surface loop of HSA.

The HSAs (including the corresponding recombinant animal albumins) described herein have a polypeptide sequence that replaces a surface loop of the native albumin (i.e., it replaces one of the surface loops of HSA described herein or an equivalent loop of a corresponding animal albumin).

Occurrence of disulfide bond bounding the polypeptide sequence that replaces a surface loop of HSA is significant, in that the presence of the disulfide bond tends to limit both the effect of the inserted sequence on the normal structure (and the corresponding biochemical and biological functions) of HSA and the effect of non-replaced HSA protein conformation on the structure (and the corresponding biochemical and biological functions) of the polypeptide sequence that replaces the surface loop of the HSA. In this way, the rHSA proteins described herein can be considered to have a modular structure, wherein the rHSA retains most of the modules (especially the non-surface modules) of naturally-occurring HSA and also includes one or more modules (having molecular- or cellular-targeting function, for example) on the surface of the HSA. The rHSA proteins thereby retain the fatty acid-complexing and other normal biochemical and biological properties of HSA, while also exhibiting the properties (e.g., cell- or molecule-targeting) properties of the module(s) installed in place of an HSA surface loop.

An rHSA that exhibits a molecular or cellular targeting function is made by exchanging a functional polypeptide sequence (e.g., a fragment of a protein that mediates an interaction between a protein and either a target protein or some other target molecule) in place of a surface loop of HSA. Manufacture of fusion proteins is well known in the art. In the context of the HSA-containing complexes described herein, the fusion protein should be a protein that retains substantially all of the primary amino acid sequence of HSA and includes inserted polypeptide sequences in place of a surface loop of HSA.

An appropriate rHSA is created by inserting a functional peptide sequence in place of one or multiple surface loops of HSA. Those surface loops have been identified by others based on the crystal structure of HSA, and are illustrated diagrammatically in FIG. 2. The rHSA possesses an engineered exogenous polypeptide region that exhibits a specific binding function. Because that polypeptide region (or regions) is inserted only in place of one or more surface loops, the rHSA retains the native functions of HSA. Retention of the normal functions of HSA, as well as the normal non-immunogenicity of HSA makes the complex described herein highly desirable as a delivery vector.

An interesting feature of HSA is that none of the 17 disulfide bonds of naturally-occurring HSA extend across the three domains (I, II, and III in FIG. 2) of HSA, and all of those disulfide bonds hold adjacent alpha-helical sequences in place. This kind of folding not only stabilizes the protein but also offers a great degree of flexibility to HSA. These disulfide bonds also hold ribbon like loops that serve link alpha-helixes. The loops that are present on the surface of the protein are appropriate sites into which exogenous polypeptide sequences can be inserted, as illustrated in FIG. 3.

Because the ends of the HSA surface loops are held in place by disulfide bonds, the loops remain relative stable, even when an exogenous polypeptide sequence is inserted in place of the surface loop that normally occurs between the disulfide-linked cysteine residues. Potential conformational changes attributable to polypeptide sequence inserted within a surface loop are constrained locally by the disulfide bonds, and likely do not disturb nearby structures. It is likely for that reason that normal HSA function remains undisturbed. It can be advantageous to incorporate a polypeptide domain that has a substantially looped secondary structure or a cyclic primary structure (i.e., in the native protein or screened peptide from which the polypeptide sequence is derived) in place of a surface loop of HSA. Such domains, which retain more nearly their 'naturally-occurring' shape, are more likely to retain the native or screened function than are substantially linear polypeptides which must be bent or strained to be incorporated in place of the loop. For a polypeptide region believed to have a substantially linear conformation in its functional state or believed to have a secondary structure more complicated than the surface loop that it replaces, it can be advantageous to include a polypeptide 'linker' region (e.g., one to several glycine residues on one or both ends of the polypeptide sequence) in order to confer sufficient flexibility to the inserted polypeptide that it can take up its functional conformation. Design and insertion of such 'linker' regions is well known in the art.

It is not critical which of the HSA surface loops is used for replacement by the functional peptide sequence. The sequence can be inserted in place of one or more of the loops, and the same sequence or different functional peptide sequences can be inserted in place of different surface loops of HSA. The surface loops of HSA are delineated by the disulfide bridges that occur in naturally occurring HSA between residues 53-62, 75-91, 90-101, 168-177, 245-253, 265-279, 278-289, 360-369, 437-448, 461-477, 476-487, and 558-567 of SEQ ID NO: 1.

The format of sequence that will replace loops held by disulfide bonds is as follows.

For the surface loop represented by HSA residues 53-62: 53Cys-$Xaa_n$-62Cys.

For the surface loop represented by HSA residues 75-91: 75Cys-$Xaa_n$-90Cys-91Cys.

For the surface loop represented by HSA residues 90-101: 90Cys-91Cys-$Xaa_n$-101Cys.

For the surface loop represented by HSA residues 168-177: 168Cys169Cys-$Xaa_n$-177Cys.

For the surface loop represented by HSA residues 245-253: 245Cys246Cys-$Xaa_n$-253Cys.

For the surface loop represented by HSA residues 265-279: 265Cys-$Xaa_n$-278Cys279Cys.

For the surface loop represented by HSA residues 278-289: 278Cys279Cys-$Xaa_n$-289Cys.

For the surface loop represented by HSA residues 360-369: 360Cys361Cys-$Xaa_n$-369Cys.

For the surface loop represented by HSA residues 437-448: 437Cys438Cys-$Xaa_n$-448Cys.

For the surface loop represented by HSA residues 461-477: 461Cys-$Xaa_n$-476Cys477Cys.

For the surface loop represented by HSA residues 476-487: 476Cys477Cys-$Xaa_n$-487Cys.

For the surface loop represented by HSA residues 558-567: 558Cys559Cys-$Xaa_n$-567Cys.

In these formulae, Xaa represents any amino acid residue, and n can be from 5 to about 30 (and is preferably from 7 to 12).

With regard to functional polypeptide sequences that can be inserted into the surface loops, disulfide bonds are required to maintain and mimic proper conformation of some targeting sequences such as the RGD motif. In the RGD motif, a local disulfide link maintains the potent protein binding ability of the motif. When selecting an appropriate exogenous functional polypeptide sequence for replacement of a surface loop, the presence of a similar function-stabilizing disulfide bond is highly desirable.

The RGD motif is clearly not the only polypeptide domain that can be inserted in place of a surface loop of HSA. Any of a wide variety of known polypeptide domains can be inserted, so long as the size of the domain does not exceed a length of about 30 residues, and preferably not more than about 25 or 12 residues. Examples of suitable protein domains include the adrenomedulin domain (CRFGTC; SEQ ID NO: 6), the endothelin-1 domain (CSCSSLMDKE CVYFC; SEQ ID NO: 7), the matrix metalloproteinase 9 (MMP9) binding peptide domain (CRRHWGFEFC; SEQ ID NO: 8), the matrix metalloproteinase 2 (MMP2) binding peptide domain (CTTHWGFTLC; SEQ ID NO: 9), and aminopeptidase N binding peptide domains (CNGRCVSGCA GRC and CVCNGRMEC; SEQ ID NOs: 10 and 11, respectively) Protein domains bounded by disulfide-linked cysteine residues are particularly well-suited for insertion in place of a surface domain of HSA.

As described herein, synthetic polypeptides can be generated in the form of libraries of random or semi-random sequences, and it is beneficial if the function of such polypeptide domains is screened in a system in which the domain occurs between disulfide-linked cysteine residues on the surface of a protein, capsid, or other particle. A screened polypeptide sequence that exhibits a desirable function can be inserted in place of a surface loop of an HSA described herein.

The source of the functional polypeptide sequence inserted in place of the surface loop is not critical, so long as the appropriate targeting function of the inserted sequence can be realized. Appropriate sequences can be derived from well-studied proteins (e.g., like the integrin-binding RDG-motif of fibronectin). Such sequences can also be determined empirically, such as with sequences derived from a library of compounds can be screened for a particular target (e.g., a protein, peptide, nucleic acid, carbohydrate, or lipid). By way of example, a phage peptide display library can be constructed using known methods, wherein each phage of the library exhibits a polypeptide sequence bounded by a linked pair of cysteine residues. By screening such a library for polypeptides that exhibit a desired function (e.g., ability to bind to a selected molecular target), a sequence suitable for conferring that property to an rHSA protein can be identified and inserted in place of an HSA surface loop as described herein. A skilled artisan appreciates that further refinement of the inserted sequence can be performed by selective mutagenesis (coupled with screening for the desired function) of the sequence inserted in place of the HSA surface loop.

The surface location of the HSA surface loops is necessary in order for the exogenous functional polypeptide sequence to exert the targeting function that is desirable in the compositions described herein. In order to enhance the targeting ability, a high affinity binding exogenous sequence and an optimal mutagenesis site of HSA can be selected, for example by screening of randomly or selectively mutated clones of a polypeptide selected from among a library of cyclic polypeptide domains. Such selective mutation can include, for example, replacement of amino acid residues of the polypeptide selected from the library with similar amino acid residues. Furthermore, screening of rHSA species wherein one or a few residues of the retained HSA sequence of the rHSA that are adjacent (i.e., not within the surface loop and within about 5 residues) of the disulfide-linked cysteine residues that define the surface loop can also improve the function, for example by improving the local protein conformation in a manner beneficial to the function of the inserted polypeptide domain. Alternatively, multiple targeting sequences can be into one or more of the surface loops of HSA. A skilled artisan in this field recognizes that these manipulations are inherently empirical, yet do not require more than ordinary experimentation.

The RGD motif (Arg-Gly-Asp) is an exhaustively-studied protein motif that occurs in many extracellular matrix (ECM) proteins such as fibronectin and vitronectin. The RGD motif is recognized by integrins, a family of heterodimeric transmembrane receptors. The alpha-v-beta-3 integrin, which has an essential role in tumor angiogenesis and metastasis, has been targeted by a variety of drug delivery vehicles.

Figure 3A:
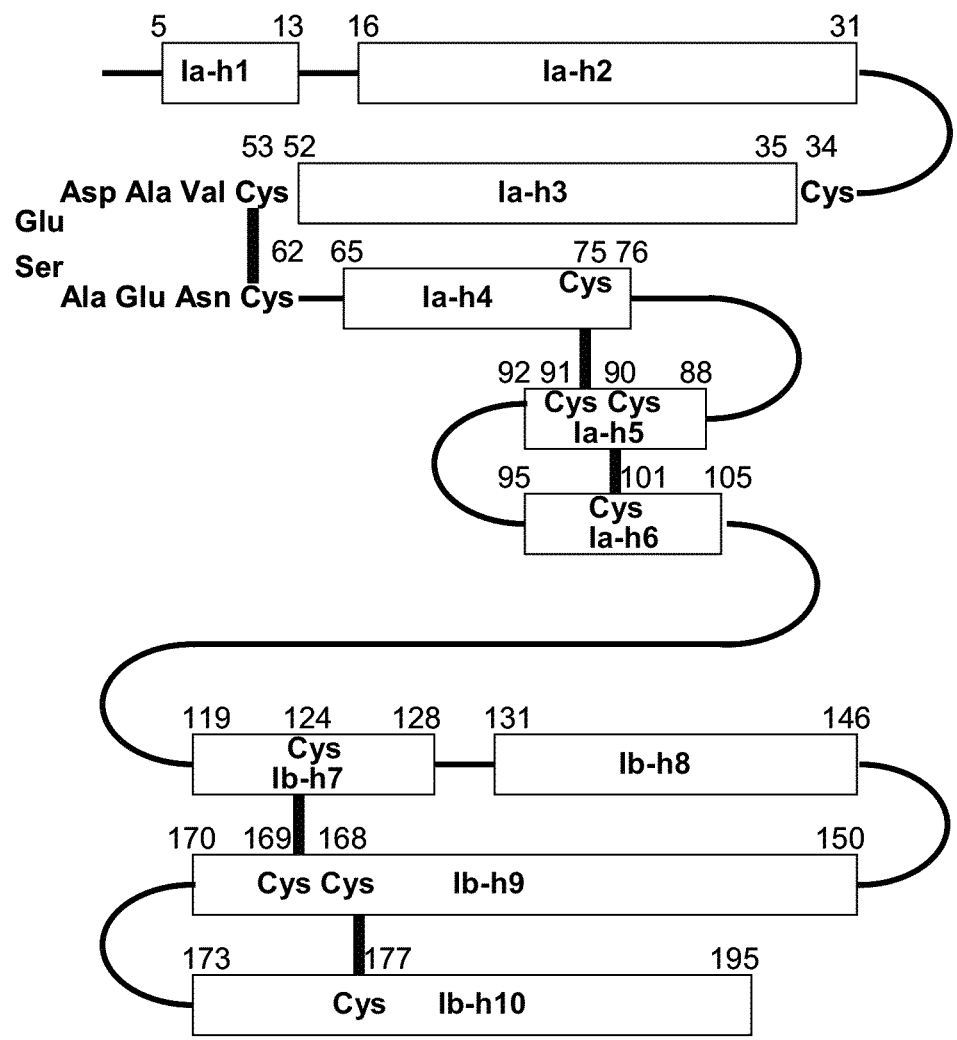
FIGS. 3A, 3B, and 3B, illustrate the structures of domains I, II, and III (respectively) of naturally-occurring HSA.
Figure 3B:
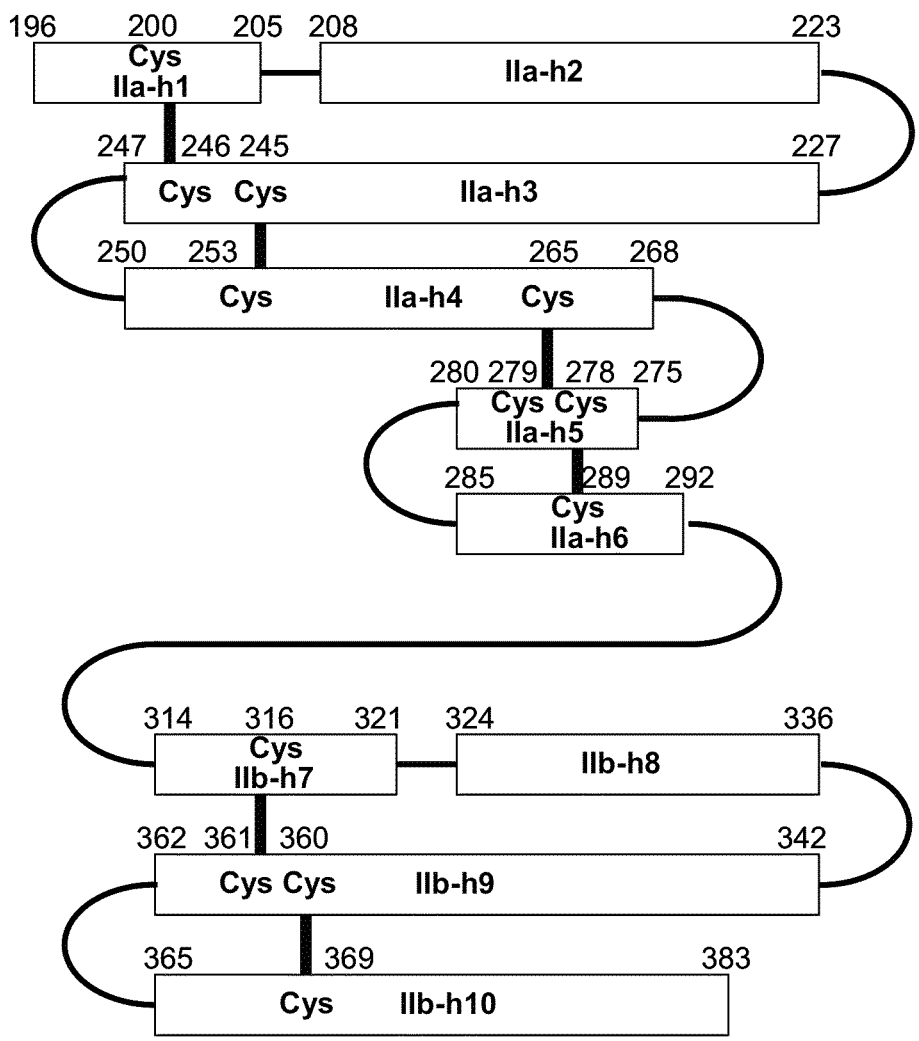
Figure 3C:
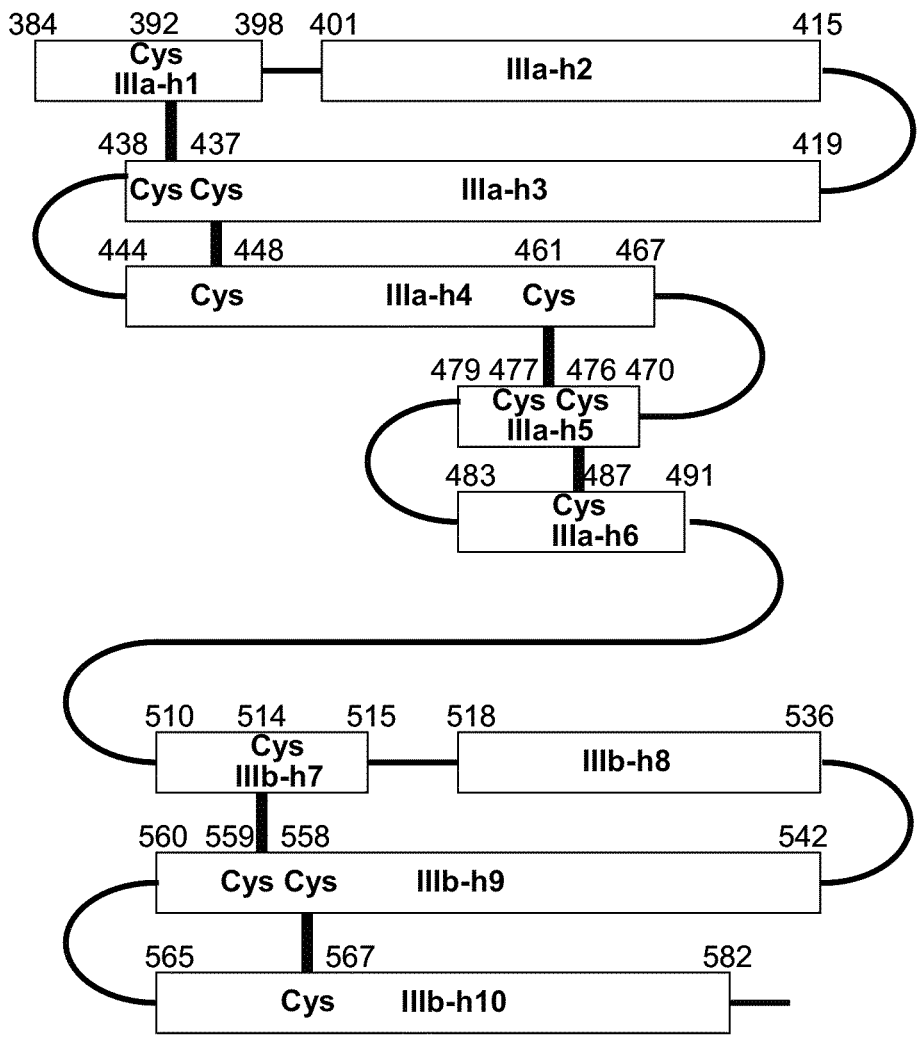
FIG. 3, consisting of FIGS. 3A, 3B, 3C, 3D, and 3E depicts HSA protein (FIGS. 3A-3C) and a recombinant HSA (rHSA.
FIGS. 3D and 3E) protein into which an exogenous RGD-motif-containing polypeptide sequence has been inserted in place of a surface loop of HSA.
Figure 3D:
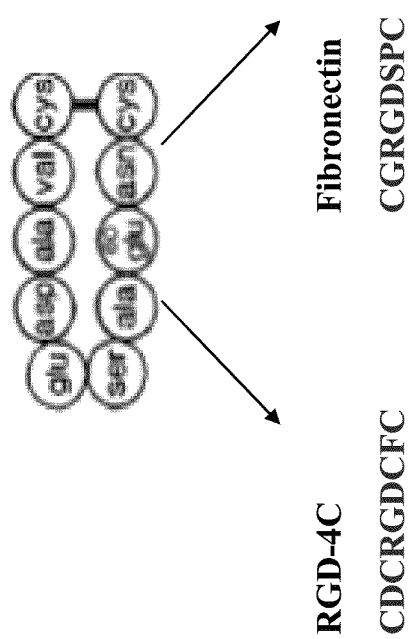

The fibronectin RGD sequence (CGRGDSPC; SEQ ID NO: 4) was inserted into HSA, replacing amino acid residues 53-62 of naturally-occurring HSA, as shown in FIGS. 3A and 3C. This fragment occurs with domain I of HSA and is located on the protein surface. Based on HSA structure and biochemical studies, these residues are not expected to have an essential role in ligand binding or protein folding. Therefore, mutations in this region should be well tolerated.

We cloned, expressed and purified this rHSA from a *Pichia pastoris* yeast rHSA expression system. The protein was soluble and was purified to apparent homogeneity. We confirmed the identity of the purified protein by Western blotting using anti-HSA antibody and anti-c-Myc antibody. The alpha-v-beta-3 integrin binding ability of RGD-HSA was confirmed by co-immunoprecipitation and Western blotting.

The HSA proteins described herein, having a polypeptide inserted in place of a surface loop of native HSA, can be used alone, in a form in which one or more molecules (e.g., a detectable marker or an affinity tag) is conjugated therewith, in a form in which the HSA is complexed with a fatty acid-conjugated molecule, in a form in which the HSA is complexed with a compound other than a fatty acid-conjugated molecule, or in a combination of these.

EXAMPLES

The invention is now described with reference to the following examples. These examples are provided for the purpose of illustration only, and the invention is not limited to these Examples, but rather encompasses all variations which are evident as a result of the teaching provided herein.

Cloning strategy to construct a Human Serum Albumin cloning vector to replace a specific loop with a functional peptide.

Figure 4:
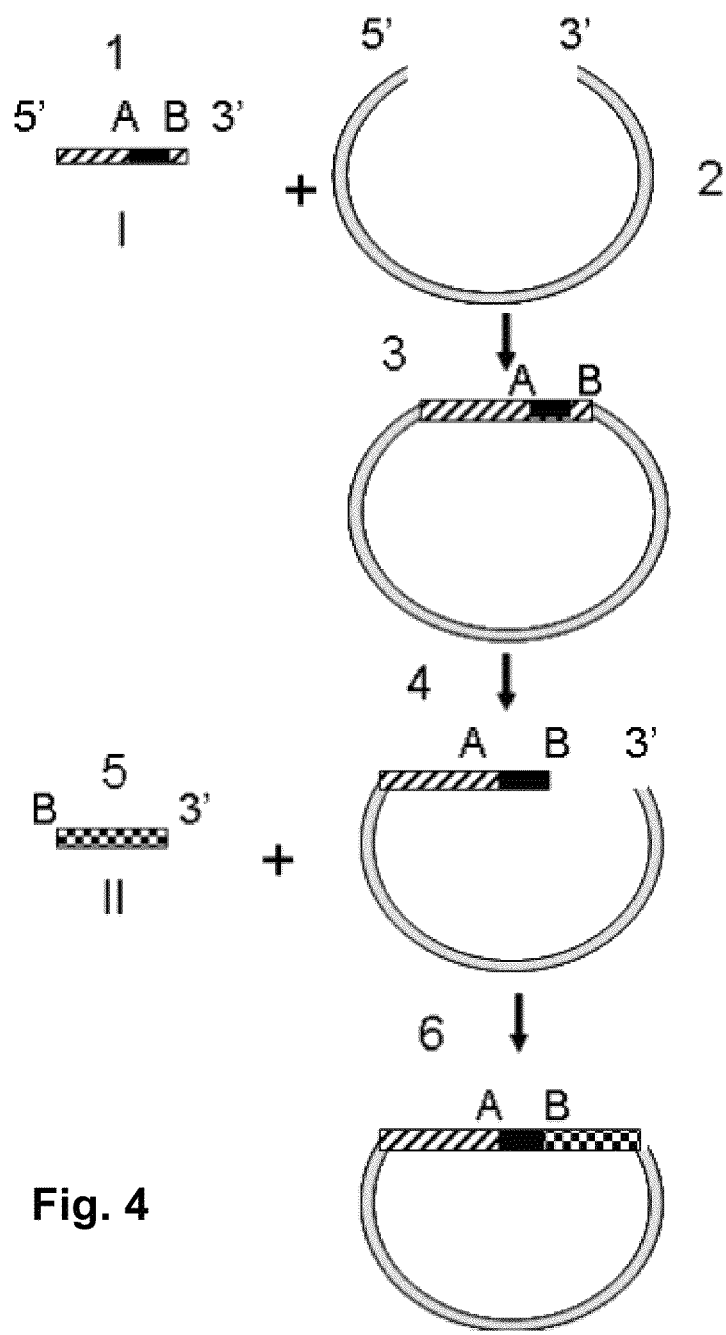
FIG. 4 is a diagram that depicts a cloning strategy described herein.

This cloning strategy is described with reference to FIG. 4. Two restriction enzyme cutting sites (A and B) close to the two cysteine residues that form a disulfide bond and hold a surface loop structure are designed and selected by changing the nucleotide coding sequence of the amino acid residues of the loop. For most cases, the generation of cloning sites A and B will only change the amino acid coding sequence but not the identity of the encoded amino acid residue. If the amino acid and its coding sequence have to be changed to generate a pair of proper cloning sites, a relative conserved amino acid at this position is selected to minimize perturbation of enzymatic activities of the mutant albumin. In addition, the cloning sites A and B can be selected at the positions of cysteine residues or either outside or inside of the loop. It is critical that these two sites must not cut the albumin gene and the cloning vector in such a way that expression of the balance of the albumin sequence is lost.

Once the cloning sites are determined, the following steps will be performed to construct the HSA cloning vector. The cloning strategy can be done using, for example, pPICZαA, B, C (INVITROGEN), pET21a, b, c (NOVAGEN) or other cloning vectors. Step 1). A gene fragment (I) of HSA that includes the DNA sequence encoding the amino-terminus of HSA through the first cysteine residue of the surface loop to be replaced is amplified by PCR. The 5' primer contains a cloning site of the vector close to 5' end of the multiple cloning sites region. The 3' primer includes the restriction enzyme cutting sites A and B and a cloning site of the vector close to the 3' end of the multiple cloning sites region. Step 2) The vector plasmid is cut with selected restriction enzymes to create the 5' and 3' cloning sites. Step 3) The fragment I from step 1 is ligated into the linearized vector. Step 4) The circular vector from step 3 is cut with selected restriction enzymes to create the B and 3' cloning sites. Step 5) A gene fragment (II) of HSA that includes the DNA sequence encoding the second cysteine residue of the surface loop to be replaced through the carboxyl-terminus of the HSA is amplified by PCR. A stop codon can be included at the end of HSA gene, or a DNA linker can be included at the end of HSA gene to add a peptide tag fragment (e.g., His$_6$ tag, c-Myc tag etc.) or construct fusion proteins. Step 6) The fragment II from step 5 is ligated into the linearized vector in step 4. A DNA sequence that encodes a functional peptide sequence can be synthesized and cloned into the A and B cloning sites of the vector obtained in step 6.

Figure 5:
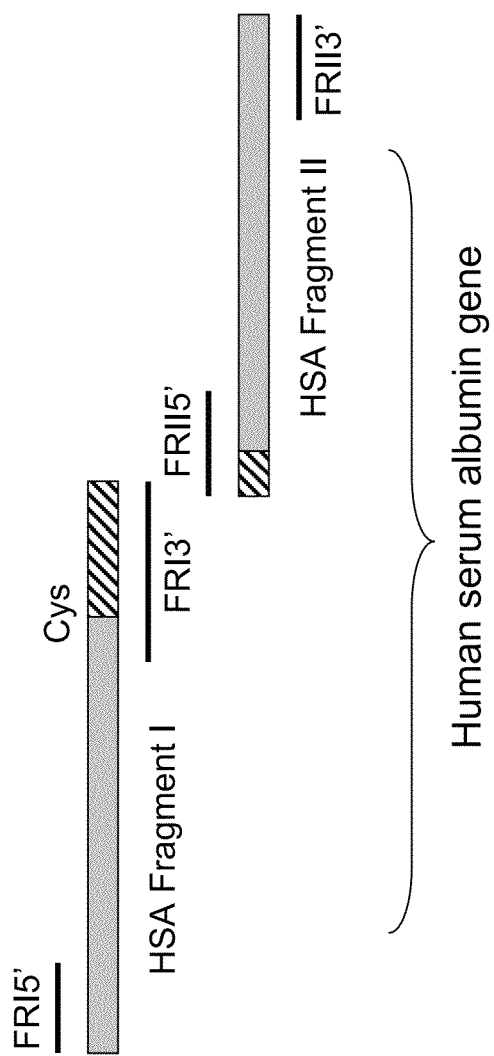
FIG. 5 is a diagram that depicts primers for use in a cloning strategy described herein.

FIG. 5 shows an arrangement of PCR primers useful in the construction of an expression vector for generating a recombinant human albumin using pPICZαA vector (INVITROGEN). In the figure, replacement of a specific albumin loop with a functional peptide is achieved as follows. Two cloning sites encompassing the loop to be replaced are created in the human serum albumin gene. Using these two universal modules, a variety of peptides can be inserted between the two cysteines and form a surface loop. To create these two cloning sites, the HSA gene is divided into two fragments, i) HSA Fragment I, which ranges from the 5' end of the gene to the position of the first cysteine residue of the loop and ii) HSA Fragment II, which ranges from the cloning site near the second cysteine residue of the loop to the 3' end of the gene. In FIG. 5, FRI5' and FRI3' stand for the 5' and 3' primers used to amplify (by PCR) the HSA Fragment I, respectively. The FRII5' and FRII3' stand for the 5' and 3' primers used to amplify the HAS Fragment II, respectively. For all loops, the common FRI5' and FRII3' primers can be used. The FRI3' and FRII5' are determined based on the location of the loop, as shown in FIGS. 6-17.

Figure 6A:
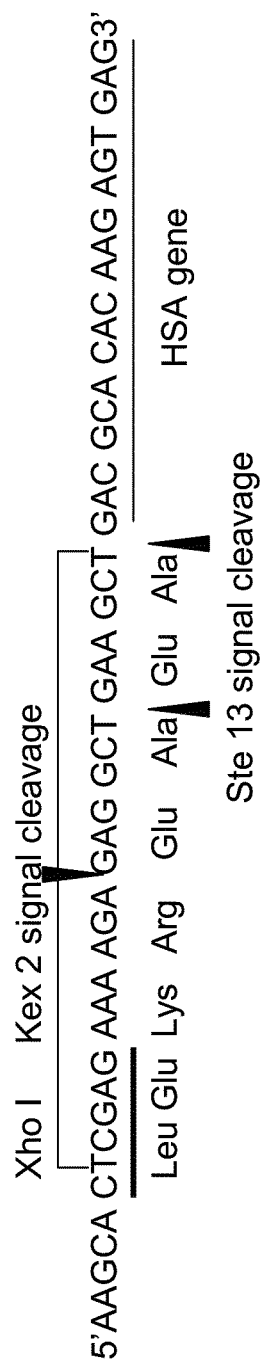
FIG. 6A shows the sequence (SEQ ID NO: 12) of the FRI5' primer.
Figure 6B:
FIG. 6B shows the sequence (SEQ ID NO: 13) of a variant of this primer.

FIG. 6A shows the sequence (SEQ ID NO: 12) of the FRI5' primer. The pPICZαA vector is for the secreting expression of protein. The Xho I cloning site is used to generate the 5' sticky end DNA. For the purpose of construction of a N-terminal albumin fusion protein using this vector, two cloning sites, EcoR I and Pml I can be included between the Ste 12 cleavage site and the 5' of HSA gene. This variant is shown in FIG. 6B.

Appropriate sequences for FRII3' primers are shown in FIG. 7. The Sac II cloning site is chosen as the 3' end cloning site. Other cloning sites such as Not I, Xba I and Sal I can also be selected for the cloning purpose, as shown in FIG. 7A. To obtain a targeting albumin with a C-terminal tag (c-Myc and His6) attached to the pPICZαA vector, a primer as shown in FIG. 7B can be used. To obtain a targeting albumin with a cloning site for a C-terminal albumin fusion protein, a primer as shown in FIG. 7C can be used.

Primers corresponding to the loop between residues 53-62 of HSA are shown in FIG. 8. The primer shown in FIG. 8A is a FRI3' primer, and the Fsp I cloning site changes the C53V54 to C53A54 (i.e., cysteine residue at position 53 and valine residue at position 54 to a cysteine residue at position 53 and alanine residue at position 54; similar terminology is used herein without this detailed explanation in each instance, the single-letter amino acid codes being well known). The primer shown in FIG. 8B is a FRII5'-1 primer, and the Sph I cloning site changes the N61C62 to A61C62. The primer shown in FIG. 8C is a FRII5'-2 primer, and the Hind III cloning site changes the coding sequence of K73L74 from AAA TAA (SEQ ID NO: 20) to AAG CTT (SEQ ID NO: 21).

Primers corresponding to the loop between residues 75-90 of HSA are shown in FIG. 9. The primer shown in FIG. 9A is a FRI3' primer, and the Fsp I cloning site changes the C75V76 to C75A76. The primer shown in FIG. 9B is a FRII5'-1 primer, and the Sph I cloning site changes the D90C91 to A90C91. The primer shown in FIG. 9C is a FRII5'-2 primer, and the Nhe I cloning site changes the A92K93 to A92S93.

Primers corresponding to the loop between residues 91-101 of HSA are shown in FIG. 10. The primer shown in FIG. 10A is a FRI3' primer, and the Fsp I cloning site changes the coding sequence of C91A93 from TGT GCA (SEQ ID NO: 28) to TGC GCA (SEQ ID NO: 29). The primer shown in FIG. 10B is a FRII5'-1 primer, and the Sph I cloning site changes the E100C101 to A100C101. The primer shown in FIG. 10C is a FRII5'-2 primer, and the Hind III cloning site changes F102L103 TO K102L103.

Primers corresponding to the loop between residues 169-177 of HSA are shown in FIG. 11. The primer shown in FIG. 11A is a FRI3' primer, and the Fsp I cloning site changes the C169Q170 TO C169A170. The primer shown in FIG. 11B is a FRII5'-1 primer, and the Sph I cloning site changes the coding sequence of A176C177 from GCC TGC (SEQ ID NO: 30) to GCA TGC (SEQ ID NO: 31). The primer shown in FIG. 11C is a FRII5'-2 primer, and the Hind III cloning site changes coding sequence of K181L182 from AAG CTC (SEQ ID NO: 32) to AAG CTT (SEQ ID NO: 33).

Primers corresponding to the loop between residues 265-278 of HSA are shown in FIG. 12. The primer shown in FIG. 12A is a FRI3' primer, and the Fsp I cloning site changes the C265E266 to C265A266. The primer shown in FIG. 12B is a FRII5'-1 primer, and the Sph I cloning site changes the E277C278 to A277C278. The primer shown in FIG. 12C is a FRII5'-2 primer, and the Nhe I cloning site changes the K286S287 to A286S287.

Primers corresponding to the loop between residues 279-289 of HSA are shown in FIG. 13. The primer shown in FIG. 13A is a FRI3' primer, and the Fsp I cloning site changes the C279E280 to C279A280. The primer shown in FIG. 13B is a FRII5'-1 primer, and the Sph I cloning site changes the H288C289 to A288C289. The primer shown in FIG. 13C is a FRII5'-2 primer, and the Nhe I cloning site changes the A291E292 to A291S292.

Primers corresponding to the loop between residues 361-369 of HSA are shown in FIG. 14. The primer shown in FIG. 14A is a FRI3' primer, and the Fsp I cloning site changes coding sequence of C361A362 from TGTGCC (SEQ ID NO: 46) to TGCGCA (SEQ ID NO: 47). The primer shown in FIG. 14B is a FRII5'-1 primer, and the Sph I cloning site changes the E368C369 to A368C369. The primer shown in FIG. 14C is a FRII5'-2 primer, and the Nhe I cloning site changes the A371K372 to A371S372.

Primers corresponding to the loop between residues 438-448 of HSA are shown in FIG. 15. The primer shown in FIG. 15A is a FRI3' primer, and the Fsp I cloning site changes the C438K439 to C438A439. The primer shown in FIG. 15B is a FRII5'-1 primer, and the Sph I cloning site changes the P447C448 to A447C448. The primer shown in FIG. 15C is a FRII5'-2 primer, and the Nhe I cloning site changes the L453S454 to A453S454.

Primers corresponding to the loop between residues 461-467 of HSA are shown in FIG. 16. The primer shown in FIG. 16A is a FRI3' primer, and the Fsp I cloning site changes the C461V462 to C461A462. The primer shown in FIG. 16B is a FRII5'-1 primer, and the Sph I cloning site changes the K475C476 to A475C476. The primer shown in FIG. 16C is a FRII5'-2 primer, and the Hind III cloning site changes the coding sequence of E478S479L480 from GAATCCTTG (SEQ ID NO: 52) to GAAAGCTTG (SEQ ID NO: 53).

A primer and a HSA II fragment corresponding to the loop between residues 559-567 of HSA are shown in FIG. 17. The primer shown in FIG. 17A is a FRI3' primer, and the Fsp I cloning site changes the 559C560K to 559C560A. Shown in FIG. 17 B is an HSA fragment useful for making rHSAs having this loop replaced by another polypeptide.

If the Hind III site is used to construct the HSA fragment II, the Hind III site of pPICZαA at the position of 872-877 is eliminated first. That is, 871 CAAGCTTGTT 880 (SEQ ID NO: 56) is changed to 871 CAAGCATGTT 880 (SEQ ID NO: 57) by site-directed mutagenesis.

Because loops located between residues 124-169, 200-246, 245-253, 316-361, 392-438, 467-487, and 514-559 either are not exposed to the surface or are too long to form a simple structure, these loops are not considered preferable candidates to swap with a functional peptide. However, if a domain of albumin instead of a whole protein is used to construct a targeting protein, these loops may become surface loops. Therefore, similar strategy can be applied to replace these loops with a functional peptide.

The primers and cloning strategies described in this section are designed based on the pPICZαA cloning vector. These strategies are also applicable to other cloning vectors. The cloning sites encompassing a designated loop are selected based on the multiple cloning sites of a vector.

It was demonstrated that recombinant wild type HSA and RGD-containing HSAs (exhibit comparable fatty acids binding abilities. BODIPY fatty acids (Invitrogen, D3823, 20 pmol) were incubated at 20 C with 0.2 or 5 micrograms of HSA in 10 µl buffer with 20 mM Tris-HCl (pH 6.8) and 150 mM NaCl for 15 minutes. The mixtures were then added with 3 µl of loading buffer (20 mM Tris-HCl (pH 6.8) and 150 mM NaCl with 50% sucrose) and loaded to 1×TBE acrylamide gel. The products were separated under 12 mA for 45 minutes. The gel was visualized under 352 nm UV. Comparable degrees of fatty acid binding were observed.

Figure 18:
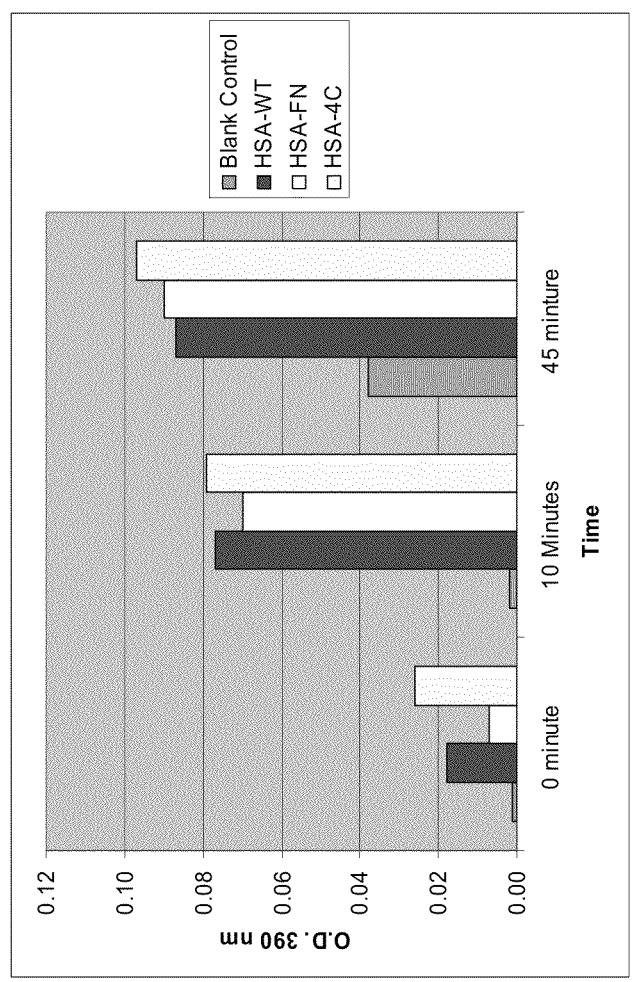
FIG. 18 is a bar graph that shows the results of esterase assays described herein.

Recombinant wild type HSA and RGD-containing HSAs (HSA-FN and HSA-4C, respectively) were shown to exhibit comparable esterase activities. The reaction of p-nitrophenyl acetate hydrolysis-mediated by rHSA and RGD-rHSA was assessed spectrophotometrically at 390 nm by monitoring the appearance of p-nitrophenol. The reaction mixtures contained 5 µM p-nitrophenyl acetate and 40 µg protein in 67 mM phosphate buffer (pH 7.4). Reactions were performed at 37° C. The results of these assays are shown in FIG. 18.

Figure 19:
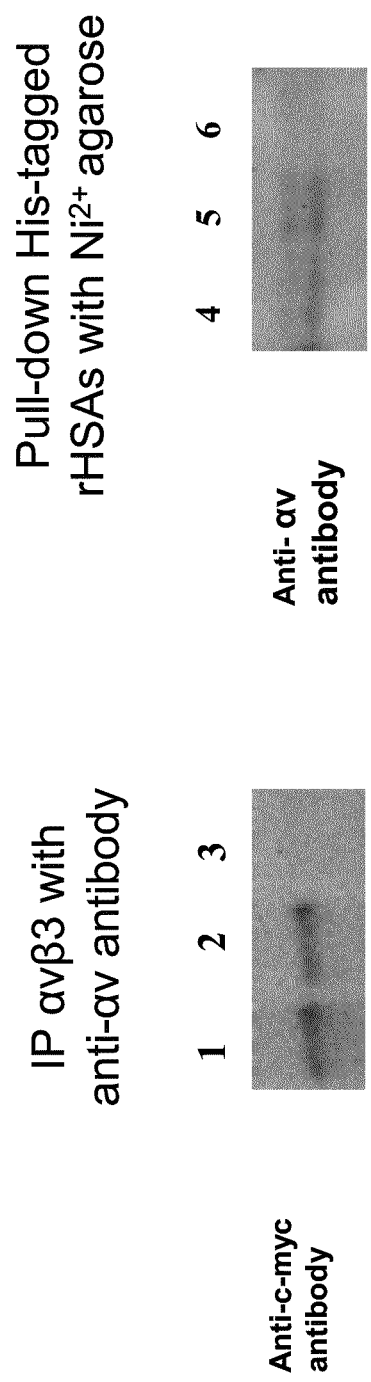
FIG. 19 shows the results of an αvβ3 (alpha v beta 3) integrin-binding assay described herein.

The ability of recombinant RGD-containing HSAs to interact with αvβ3 integrin was demonstrated. The results of this assay are shown in FIG. 19. Lanes 1 and 4 each contained a mixture of 300 µg MDA-MD-435S (αvβ3 positive) cell extract and 1.2 µg of RGD-rHSA-FN (rHSA containing fibronectin RGD sequence). Lanes 2 and 5 each contained a mixture of 300 µg MDA-MD435S cell extract and 1.2 µg of RGD-rHSA-4C (rHSA containing RGD sequence held by two pairs of disulfide bonds). Lanes 3 and 6 each contained mixture of 300 µg MDA-MD435S cell extract and 1.2 µg of RGD-rHSA (wild type HSA). For the convenience of purification and detection, all rHSAs were fused with c-terminal c-myc and His$_6$ tags. For lane 1, 2, and 3, the αvβ3 complexes were immunoprecipitated with anti-αv antibody (CHEMICON, AB1930). rHSAs associated with αvβ3 were detected by anti-c-myc antibody. The wild type rHSA was not detectable. For lane 4,5, and 6, the poly-HIS-tagged rHSAs were pulled down with Ni2+-charged chelating agarose. αvβ3 Associated with αvβ3 was detected by anti-αv antibody (CHEMICON, AB 1930). Because the wild type rHSA does not interact with αvβ3 integrin, αv was not detectable at lane 6.

RGD-containing rHSAs were demonstrated to facilitate albumin-mediated uptake and/or binding of αvβ3 positive MDA-MB-435S cells. rHSAs were labeled with NHS-Rhodamine (PIERCE 46102) at primary amines following manufacturer protocols. The products were thoroughly dialyzed and desalted to remove free Rhodamine. The fluorescent dye labeled rHSAs (50 pmol for rHSA, RGD-rHSA-FN and RGD-rHSA-4C) were added to cultured MDA-MB-435S cells (with 250 µl L-15 medium in 24-well plate). Cellular uptake and/or binding was monitored at 1, 2, 4, and 8 hours after washing with fresh un-labeled medium. Cellular uptake of albumin was then visualized by fluorescent microscopy. Cellular uptake and/or binding of RGD-containing rHSAs could be clearly seen at the first hour. This process was difficult to observe for wild type rHSA at this point. However, albumin uptake for wild type rHSA could be observed after 4 hours of incubation. Cellular uptake/binding of wt rHSA was still significantly lower that that of RGD-containing rHSAs. The Rhodamine-labeled RGD-containing rHSA evenly distributed inside the cell with centered bright dots. These results suggest that the endocytosis contributes significantly to cellular uptake.

Albumin uptake and/or binding of rHSAs in HeLa cells was also demonstrated. The RGD sequence of RGD-rHSA-FN and RGD-rHSA-4C mildly stimulated albumin uptake and/or binding in HeLa cells. However, this effect was not as significant as the effects observed in MDA-MB-435S cells. These observations suggested a cell type-dependent function of RGD-rHSAs. It has been reported that there is no αvβ3 type of integrin in HeLa cells. Nonetheless, HeLa cells are still able to bind fibronectin. Similar to the cellular uptake experiments for MDA-MB-435S cells, the fluorescent dye labeled rHSAs (50 pmol for rHSA, RGD-rHSA-FN and RGD-rHSA-4C) were added to cultured HeLa cells (with 250 µl EMEM in 24-well plate). Cellular uptake and/or binding was monitored at 1, 4, and 8 hours after washing with fresh non-labeled medium. Cellular uptake and/or binding of albumin was then visualized using fluorescent microscopy. Cellular uptake and/or binding of RGD-containing rHSAs and wt rHSA could be clearly observed at the first hour. This experiment suggests that cellular uptake of albumin occurs for certain tumor cells. RGD binding and cellular uptake of albumin will both benefit the albumin-mediated siRNA transfection in vitro and in viva.

HSA was demonstrated to augment cellular uptake of fatty acid. BODIPY fatty acids (Invitrogen, D3823, 200 pmol) were incubated at 20° C. with 1 µmol of defatted HSA or without HSA in 20 µl buffer with 20 mM Tris-HCl (pH 6.8) and 150 mM NaCl for 15 minutes. The mixtures were then added to HeLa cells in 200 µl of EMEM. After washing the cells with fresh medium, cellular uptake and/or binding was visualized using fluorescent microscopy after 12 hours of incubation. Cells incubated with defatted HSA exhibited more fatty acid uptake and/or binding than cells incubated without HSA. These results suggest that HSA can form a complex with the fatty acid-conjugated fluorescent probe and facilitated cellular uptake of the conjugate.

The ability of HSA to bind a fatty acid-conjugated peptide was demonstrated. A peptide designated faTraE (CHLDAH-WKG; SEQ ID NO: 58) was conjugated with fluorescein at the position of primary amine of Lys through MHS ester (synthesized by Sigma). This peptide (500 µmol) was then conjugated at the thiol group of Cys with 16-methanethiosulfonyl hexadecanoic acid (Toronto Research Chemicals, Inc., 1:2 of molar ration) in an acetone nitrile mixture to form $HOOC-(CH_2)_{15}-S-S$-peptide. The product was vacuum dried and resuspended in DMSO. The fatty acid-modified peptide (25 pmol) was incubated with defatted HSA (100 pmol) in 10 μl buffer (Tris-HCl 20 mM pH6.8 and 150 mM NaCl) for 15 minutes at room temperature. The reaction mixture was loaded to 0.5×TBE acrylamide gel and separated under 12 mA current. The fluorescein-labeled DNAs were visualized under UV 352 nm HSA complexed with the fatty acid-conjugated faTraF peptide could be clearly observed. This experiment demonstrates the feasibility of using HSAs to deliver fatty acid-modified peptides.

The ability of fatty acid-conjugated peptides to transfect HeLa cells in the presence of HSA was demonstrated. Fatty acid-conjugated faTraF peptides and non-conjugated faTraE peptides (250 pmol) were added to separate batches of HeLa cells (24-well plate with 250 μl of EMEM medium). 250 Pmol of HSA was added to the incubation of some wells, but not others. Cells incubated in the presence of HSA and the fatty-acid conjugated peptides were transfected. The transfection of unmodified peptides to HeLa cells can not be observed under these conditions. These results demonstrate the feasibility of transfecting cells using a fatty acid-conjugated transfection agent in the presence of HSA.

The ability of HSA to bind fatty acid-conjugated double stranded oligonucleotides was demonstrated. Thiol-modified 22 mer oligonucleotides ($CH_3$—$(CH_2)_5$—S—S—$(CH_2)_5$-5'-DNA) (50 μM in 100 μl of $H_2O$) were reduced to HS—$(CH_2)_5$-5'-DNA with 10 mM DTT overnight at room temperature. The mixture was desalted to remove free DTT. Meanwhile, dithiodipyridine (10 μl of 10 mM in acetonitrile) was mixed with 16-mercaptohexadecanoic acids (10 μl of 10 mM in DMSO) to modify the free thiol group of 16-mercaptohexadecanoic acids. The mixture was incubated with reduced DNA at room temperature for 60 minutes. The reaction was then desalted using a G-25 centrifugal column. The fatty acid-modified single-stranded oligonucleotides were annealed with 22 mer complementary oligonucleotides labeled using the cy3 dye at their 5' ends. The fatty acid-modified and cy3-labled double stranded 22 mer oligonucleotides (25 pmol) were incubated with defatted HSA (30 pmol) in 10 μl buffer (Tris-HCl 20 mM pH6.8 and 150 mM NaCl) for 15 minutes at room temperature. The reaction was loaded to 0.5×TBE acrylamide gel and separated under 12 mA. The cy3 labeled DNAs were visualized under UV 352 nm Fatty acid-conjugated oligonucleotides complexed with HSA could be clearly visualized based on their position on the gel. These results support the feasibility of using HSAs to deliver fatty acid-modified oligonucleotides, such as siRNA. In other experiments, HSA was observed not to bind thiol-modified 22-mer oligonucleotides ($CH_3$—$(CH_2)_5$—S—S—$(CH_2)_5$-5'-DNA) or amine-modified 22-mer oligonucleotides (NH2-$(CH_2)_{12}$-5'-DNA). These results suggest that the carboxyl group of the fatty acid is critical for the binding of fatty acid-modified DNA.

The ability of fatty acid-conjugated oligonucleotides to transfect HeLa cells in the presence of HSA was demonstrated. Fatty acid-conjugated and cy3 labeled oligonucleotides (synthesized as described above; 40 pmol) were added to HeLa cells (24-well plate with 250 μl of EMEM medium) in the presence (80 pmol) and absence of HSA and the cells were incubated in those mixtures. The modified oligonucleotides were able to transfect HeLa cells. Pre-incubating fatty acid-modified DNA with HSA mildly increased transfection efficiency, as assessed by the amount and brightness of transfected cells in the assay system used. Cholesterol-modified oligonucleotides (40 pmol, ordered from IDT DNA Inc.) were able to bind HSA as well as transfect HeLa cells. However, the transfection was toxic and caused cell death. This may be related to the cellular membrane integration functions of cholesterol. In contrast, at the concentrations used here, the fatty acid-modified oligonucleotides did not exhibit cytotoxicity. As an negative control, amine-modified oligonucleotides (IDT DNA Inc.) with —$(CH_2)_{12}$-spacer were used and exhibited only barley detectable transfected cells. The results of this experiment demonstrate the feasibility of using HSA-complexed fatty acid-conjugated oligonucleotides to transfect cells.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of delivering a first molecule to a target within the body of a human, the method comprising contacting a first composition and a second composition outside the body of the human, wherein the first composition comprises a conjugate of the first molecule and a fatty acid, wherein the second composition comprises a human serum albumin, and wherein the first and second compositions are contacted for a time and under conditions sufficient for the conjugate to bind with the albumin to form a complex; and thereafter administering the complex to a tissue from which the target is accessible, whereby the first molecule is delivered to the target.

2. The method of claim 1, wherein the target is a cell.

3. The method of claim 1, wherein the target is a tissue.

4. The method of claim 1, wherein substantially all first molecules not bound with the albumin are removed from the preparation containing the complex prior to administering the preparation to the tissue.

5. The method of claim 1, wherein a preparation containing the complex is applied directly to a tissue comprising the target.

6. The method of claim 1, wherein a preparation containing the complex is applied to an endothelial tissue that separates the target from the site of application.

7. The method of claim 1, wherein a preparation containing the complex is administered systemically.

8. The method of claim 7, wherein the preparation is administered intravenously.

9. The method of claim 1, wherein the albumin is normal human serum albumin.

10. The method of claim 9, wherein the albumin is substantially purified.

11. The method of claim 9, wherein the albumin is defatted.

12. The method of claim 1, wherein the albumin is a recombinant human serum albumin.

13. The method of claim 12, wherein the recombinant albumin is a fusion protein having a ligand-binding protein domain inserted in place of a surface loop of the albumin.

14. The method of claim 13, wherein the ligand is a ligand that occurs on the surface of the cell.

15. The method of claim 13, wherein the domain is selected from the group consisting of an RGD-containing domain, an adrenomedulin domain, an endothelin-1 domain, a matrix metalloproteinase 9 binding peptide domain, a matrix metalloproteinase 2 binding peptide domain, and an aminopeptidase N binding peptide domain.

16. The method of claim 13, wherein the domain has an amino acid sequence selected from the group consisting of SEQ ID NOs: 3-11.

17. The method off claim 13, wherein the ligand is a ligand that occurs in a tissue that includes the target.

18. The method of claim 13, wherein the surface loop is selected from the group consisting of
  (i) the loop defined by residues 53-62;
  (ii) the loop defined by residues 75-91;
  (iii) the loop defined by residues 91-101;
  (iv) the loop defined by residues 168-177;
  (v) the loop defined by residues 245-253;
  (vi) the loop defined by residues 265-279;
  (vii) the loop defined by residues 278-289;
  (viii) the loop defined by residues 360-369;
  (ix) the loop defined by residues 437-448;
  (x) the loop defined by residues 461-477;
  (xi) the loop defined by residues 476-487; and
  (xii) the loop defined by residues 558-567
of SEQ ID NO: 1.

19. The method of claim 1, wherein the first molecule is selected from the group consisting of a polynucleotide, a polypeptide, and a drug other than a polynucleotide or a polypeptide.

20. The method of claim 1, wherein the first molecule is selected from the group consisting of a radiolabeled compound and an imaging agent other than a radiolabeled compound.

21. The method of claim 1, wherein the fatty acid is a $C_{10}$-$C_{20}$ fatty acid.

22. The method of claim 1, wherein the fatty acid is a $C_{16}$-$C_{20}$ fatty acid.

23. The method of claim 1, wherein the conjugate is an amide formed by condensation of a carboxylate moiety of the fatty acid and an anime moiety of the first molecule.

24. The method of claim 1, wherein the first molecule and the fatty acid are conjugated by way of a disulfide linkage.

25. The method of claim 1, further comprising binding the albumin with a second conjugate, wherein the second conjugate comprises a second fatty acid moiety conjugated with a compound that binds specifically with a target that occurs on the surface of a cell.

26. The method of claim 1, further comprising binding the albumin with a second conjugate, wherein the second conjugate comprises a second fatty acid moiety conjugated with a compound that binds specifically with a target that occurs in a tissue.

* * * * *

SEQUENCE LISTING

```
<160> NUMBER OF SEQ ID NOS: 58

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
```

```
                         85                  90                  95
Lys Leu Cys Thr Val Ala Thr Leu Arg Glu Thr Tyr Gly Glu Met Ala
                100                 105                 110
Asp Cys Cys Ala Lys Gln Glu Pro Glu Arg Asn Glu Cys Phe Leu Gln
            115                 120                 125
His Lys Asp Asp Asn Pro Asn Leu Pro Arg Leu Val Arg Pro Glu Val
        130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
                180                 185                 190
Cys Gln Ala Ala Asp Lys Ala Ala Cys Leu Leu Pro Lys Leu Asp Glu
            195                 200                 205
Leu Arg Asp Glu Gly Lys Ala Ser Ser Ala Lys Gln Arg Leu Lys Cys
        210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
                260                 265                 270
Asp Leu Leu Glu Cys Ala Asp Asp Arg Ala Asp Leu Ala Lys Tyr Ile
            275                 280                 285
Cys Glu Asn Gln Asp Ser Ile Ser Ser Lys Leu Lys Glu Cys Cys Glu
        290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
            355                 360                 365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
            435                 440                 445
Glu Val Ser Arg Asn Leu Gly Lys Val Gly Ser Lys Cys Cys Lys His
        450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
```

-continued

```
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
        595                 600                 605
Leu

<210> SEQ ID NO 2
<211> LENGTH: 10
<212> TYPE: PRT
<213> ORGANISM: Homo sapiens

<400> SEQUENCE: 2

Cys Val Ala Asp Glu Ser Ala Glu Asn Cys
1               5                   10

<210> SEQ ID NO 3
<211> LENGTH: 9
<212> TYPE: PRT
<213> ORGANISM: Homo sapiens

<400> SEQUENCE: 3

Cys Asp Cys Arg Gly Asp Cys Phe Cys
1               5

<210> SEQ ID NO 4
<211> LENGTH: 8
<212> TYPE: PRT
<213> ORGANISM: Homo sapiens

<400> SEQUENCE: 4

Cys Gly Arg Gly Asp Ser Pro Cys
1               5

<210> SEQ ID NO 5
<211> LENGTH: 9
<212> TYPE: PRT
<213> ORGANISM: Homo sapiens

<400> SEQUENCE: 5

Cys His Leu Asp Ala His Trp Lys Gly
1               5

<210> SEQ ID NO 6
<211> LENGTH: 6
<212> TYPE: PRT
<213> ORGANISM: Homo sapiens

<400> SEQUENCE: 6

Cys Arg Phe Gly Thr Cys
1               5

<210> SEQ ID NO 7
<211> LENGTH: 15
```

```
<212> TYPE: PRT
<213> ORGANISM: Homo sapiens

<400> SEQUENCE: 7

Cys Ser Cys Ser Ser Leu Met Asp Lys Glu Cys Val Tyr Phe Cys
1               5                   10                  15

<210> SEQ ID NO 8
<211> LENGTH: 10
<212> TYPE: PRT
<213> ORGANISM: Homo sapiens

<400> SEQUENCE: 8

Cys Arg Arg His Trp Gly Phe Glu Phe Cys
1               5                   10

<210> SEQ ID NO 9
<211> LENGTH: 10
<212> TYPE: PRT
<213> ORGANISM: Homo sapiens

<400> SEQUENCE: 9

Cys Thr Thr His Trp Gly Phe Thr Leu Cys
1               5                   10

<210> SEQ ID NO 10
<211> LENGTH: 13
<212> TYPE: PRT
<213> ORGANISM: Homo sapiens

<400> SEQUENCE: 10

Cys Asn Gly Arg Cys Val Ser Gly Cys Ala Gly Arg Cys
1               5                   10

<210> SEQ ID NO 11
<211> LENGTH: 9
<212> TYPE: PRT
<213> ORGANISM: Homo sapiens

<400> SEQUENCE: 11

Cys Val Cys Asn Gly Arg Met Glu Cys
1               5

<210> SEQ ID NO 12
<211> LENGTH: 47
<212> TYPE: DNA
<213> ORGANISM: Artificial
<220> FEATURE:
<223> OTHER INFORMATION: FRI5' Primer

<400> SEQUENCE: 12
aagcactcga gaaaagagag gctgaagctg acgcacacaa gagtgag          47

<210> SEQ ID NO 13
<211> LENGTH: 59
<212> TYPE: DNA
<213> ORGANISM: Artificial
<220> FEATURE:
<223> OTHER INFORMATION: Variant of FRI5' Primer

<400> SEQUENCE: 13
aagcactcga gaaaagagag gctgaagctg aatcccacgt ggacgcacac aagagtgag     59

<210> SEQ ID NO 14
<211> LENGTH: 35
```

-continued

```
<212> TYPE: DNA
<213> ORGANISM: Artificial
<220> FEATURE:
<223> OTHER INFORMATION: FRII3' Primer

<400> SEQUENCE: 14
cgtaaccgcg gtcataagcc taaggcagct tgact                          35

<210> SEQ ID NO 15
<211> LENGTH: 33
<212> TYPE: DNA
<213> ORGANISM: Artificial
<220> FEATURE:
<223> OTHER INFORMATION: FRII3' Primer

<400> SEQUENCE: 15
cgtaaccgcg gctaagccta aggcagcttg act                            33

<210> SEQ ID NO 16
<211> LENGTH: 41
<212> TYPE: DNA
<213> ORGANISM: Artificial
<220> FEATURE:
<223> OTHER INFORMATION: FRII3' Primer

<400> SEQUENCE: 16
cgtaaccgcg gtcaactagt taagcctaag gcagcttgac t                   41

<210> SEQ ID NO 17
<211> LENGTH: 56
<212> TYPE: DNA
<213> ORGANISM: Artificial
<220> FEATURE:
<223> OTHER INFORMATION: FRI3' Primer

<400> SEQUENCE: 17
cgtaaccgcg ggcatgcgct agcaagcttt gcgcatgttt ttgcaaattc agttac   56

<210> SEQ ID NO 18
<211> LENGTH: 32
<212> TYPE: DNA
<213> ORGANISM: Artificial
<220> FEATURE:
<223> OTHER INFORMATION: FRII 5' Primer

<400> SEQUENCE: 18
cctatgcatg cgacaaatca cttcataccc tt                             32

<210> SEQ ID NO 19
<211> LENGTH: 32
<212> TYPE: DNA
<213> ORGANISM: Artificial
<220> FEATURE:
<223> OTHER INFORMATION: FRII 5' Primer

<400> SEQUENCE: 19
cctataagct ttgcacagtt gcaactcttc gt                             32

<210> SEQ ID NO 20
<211> LENGTH: 6
<212> TYPE: DNA
<213> ORGANISM: Artificial
<220> FEATURE:
<223> OTHER INFORMATION: FRII5'-2 primer Hind III cloning site prior to
      change

<400> SEQUENCE: 20
```

-continued

```
aaataa                                                            6

<210> SEQ ID NO 21
<211> LENGTH: 6
<212> TYPE: DNA
<213> ORGANISM: Artificial
<220> FEATURE:
<223> OTHER INFORMATION: FRII5'-2 primer Hind III cloning site after
      change

<400> SEQUENCE: 21 aagctt                                                            6

<210> SEQ ID NO 22
<211> LENGTH: 59
<212> TYPE: DNA
<213> ORGANISM: Artificial
<220> FEATURE:
<223> OTHER INFORMATION: FRI3' Primer

<400> SEQUENCE: 22
cgtaaccgcg ggcatgcgct agcaagcttt gcgcataatt tgtctccaaa aagggtatg    59

<210> SEQ ID NO 23
<211> LENGTH: 32
<212> TYPE: DNA
<213> ORGANISM: Artificial
<220> FEATURE:
<223> OTHER INFORMATION: FRII 5' Primer

<400> SEQUENCE: 23
cctatgcatg ctgtgcaaaa caagaacctg ag                                32

<210> SEQ ID NO 24
<211> LENGTH: 35
<212> TYPE: DNA
<213> ORGANISM: Artificial
<220> FEATURE:
<223> OTHER INFORMATION: FRII 5' Primer

<400> SEQUENCE: 24
cctatgctag ccaagaacct gagagaaatg aatgc                             35

<210> SEQ ID NO 25
<211> LENGTH: 56
<212> TYPE: DNA
<213> ORGANISM: Artificial
<220> FEATURE:
<223> OTHER INFORMATION: FRI3' Primer

<400> SEQUENCE: 25
cgtaaccgcg ggcatgcgct agcaagcttt gcgcagcagt cagccatttc accata       56

<210> SEQ ID NO 26
<211> LENGTH: 32
<212> TYPE: DNA
<213> ORGANISM: Artificial
<220> FEATURE:
<223> OTHER INFORMATION: FRII 5' Primer

<400> SEQUENCE: 26
cctatgcatg cttcttgcaa cacaaagatg ac                                32

<210> SEQ ID NO 27
<211> LENGTH: 32
```

```
<212> TYPE: DNA
<213> ORGANISM: Artificial
<220> FEATURE:
<223> OTHER INFORMATION: FRII 5' Primer

<400> SEQUENCE: 27
cctataagct tcaacacaaa gatgacaacc cc                                    32

<210> SEQ ID NO 28
<211> LENGTH: 6
<212> TYPE: DNA
<213> ORGANISM: Artificial
<220> FEATURE:
<223> OTHER INFORMATION: FSP I cloning site of FRI3' primer prior to
      change

<400> SEQUENCE: 28 tgtgca                                                                  6

<210> SEQ ID NO 29
<211> LENGTH: 6
<212> TYPE: DNA
<213> ORGANISM: Artificial
<220> FEATURE:
<223> OTHER INFORMATION: Fsp I cloning stie of FRI3' primer after change

<400> SEQUENCE: 29 tgcgca                                                                  6

<210> SEQ ID NO 30
<211> LENGTH: 6
<212> TYPE: DNA
<213> ORGANISM: Artificial
<220> FEATURE:
<223> OTHER INFORMATION: Sph I cloning site of FRII5'-1 primer prior to
      change

<400> SEQUENCE: 30 gcctgc                                                                  6

<210> SEQ ID NO 31
<211> LENGTH: 6
<212> TYPE: DNA
<213> ORGANISM: Artificial
<220> FEATURE:
<223> OTHER INFORMATION: Sph I cloning site of FRII5'-1 primer after
      change

<400> SEQUENCE: 31 gcatgc                                                                  6

<210> SEQ ID NO 32
<211> LENGTH: 6
<212> TYPE: DNA
<213> ORGANISM: Artificial
<220> FEATURE:
<223> OTHER INFORMATION: Hind III cloining site of FRII5'-2 primer prior
      to change

<400> SEQUENCE: 32 aagctc                                                                  6

<210> SEQ ID NO 33
<211> LENGTH: 6
<212> TYPE: DNA
<213> ORGANISM: Artificial
<220> FEATURE:
```

```
<223> OTHER INFORMATION: Hind III cloning site of FRII5'-2 primer after
      change

<400> SEQUENCE: 33 aagctt                                                                  6

<210> SEQ ID NO 34
<211> LENGTH: 56
<212> TYPE: DNA
<213> ORGANISM: Artificial
<220> FEATURE:
<223> OTHER INFORMATION: FRI3' Primer

<400> SEQUENCE: 34
cgtaaccgcg ggcatgcgct agcaagcttt gcgcaacatt ctgtaaaagc agcttt         56

<210> SEQ ID NO 35
<211> LENGTH: 32
<212> TYPE: DNA
<213> ORGANISM: Artificial
<220> FEATURE:
<223> OTHER INFORMATION: FRII 5' Primer

<400> SEQUENCE: 35
cctatgcatg cctgttgcca aagctcgatg aa                                    32

<210> SEQ ID NO 36
<211> LENGTH: 35
<212> TYPE: DNA
<213> ORGANISM: Artificial
<220> FEATURE:
<223> OTHER INFORMATION: FRII 5' Primer

<400> SEQUENCE: 36
cctatgctag ccaagaacct gagagaaatg aatgc                                 35

<210> SEQ ID NO 37
<211> LENGTH: 56
<212> TYPE: DNA
<213> ORGANISM: Artificial
<220> FEATURE:
<223> OTHER INFORMATION: FRI3' Primer

<400> SEQUENCE: 37
cgtaaccgcg ggcatgcgct agcaagcttt gcgcagatat acttggcaag gtccgc         56

<210> SEQ ID NO 38
<211> LENGTH: 32
<212> TYPE: DNA
<213> ORGANISM: Artificial
<220> FEATURE:
<223> OTHER INFORMATION: FRII 5' Primer

<400> SEQUENCE: 38
cctatgcatg ctgtgaaaaa cctctgttgg aa                                    32

<210> SEQ ID NO 39
<211> LENGTH: 32
<212> TYPE: DNA
<213> ORGANISM: Artificial
<220> FEATURE:
<223> OTHER INFORMATION: FRII 5' Primer

<400> SEQUENCE: 39
cctatgctag ccactgcatt gccgaagtgg aa                                    32
```

<210> SEQ ID NO 40
<211> LENGTH: 56
<212> TYPE: DNA
<213> ORGANISM: Artificial
<220> FEATURE:
<223> OTHER INFORMATION: FRI3' Primer

<400> SEQUENCE: 40
cgtaaccgcg ggcatgcgct agcaagcttt gcgcagcatt ccttcagttt actgga    56

<210> SEQ ID NO 41
<211> LENGTH: 32
<212> TYPE: DNA
<213> ORGANISM: Artificial
<220> FEATURE:
<223> OTHER INFORMATION: FRII 5' Primer

<400> SEQUENCE: 41
cctatgcatg cattgccgaa gtggaaaatg at                               32

<210> SEQ ID NO 42
<211> LENGTH: 32
<212> TYPE: DNA
<213> ORGANISM: Artificial
<220> FEATURE:
<223> OTHER INFORMATION: FRII 5' Primer

<400> SEQUENCE: 42
cctatgctag cgtggaaaat gatgagatgc ct                               32

<210> SEQ ID NO 43
<211> LENGTH: 56
<212> TYPE: DNA
<213> ORGANISM: Artificial
<220> FEATURE:
<223> OTHER INFORMATION: FRI3' Primer

<400> SEQUENCE: 43
cgtaaccgcg ggcatgcgct agcaagcttt gcgcagcact tctctagagt ggtttc    56

<210> SEQ ID NO 44
<211> LENGTH: 38
<212> TYPE: DNA
<213> ORGANISM: Artificial
<220> FEATURE:
<223> OTHER INFORMATION: FRII 5' Primer

<400> SEQUENCE: 44
cctatgcatg ctatgccaaa gtgttcgatg aatttaaa                         38

<210> SEQ ID NO 45
<211> LENGTH: 32
<212> TYPE: DNA
<213> ORGANISM: Artificial
<220> FEATURE:
<223> OTHER INFORMATION: FRII 5' Primer

<400> SEQUENCE: 45
cctatgctag cgtgttcgat gaatttaaac ct                               32

<210> SEQ ID NO 46
<211> LENGTH: 56
<212> TYPE: DNA
<213> ORGANISM: Artificial
<220> FEATURE:
<223> OTHER INFORMATION: FRI3' Primer

<400> SEQUENCE: 46
cgtaaccgcg ggcatgcgct agcaagcttt gcgcaacatt tgctgcccac ttttcc        56

<210> SEQ ID NO 47
<211> LENGTH: 32
<212> TYPE: DNA
<213> ORGANISM: Artificial
<220> FEATURE:
<223> OTHER INFORMATION: FRII 5' Primer

<400> SEQUENCE: 47
cctatgcatg cgcagaagac tatctatccg tg        32

<210> SEQ ID NO 48
<211> LENGTH: 31
<212> TYPE: DNA
<213> ORGANISM: Artificial
<220> FEATURE:
<223> OTHER INFORMATION: FRII 5' Primer

<400> SEQUENCE: 48
cctatgctag cgtggtcctg aacagttatg t        31

<210> SEQ ID NO 49
<211> LENGTH: 56
<212> TYPE: DNA
<213> ORGANISM: Artificial
<220> FEATURE:
<223> OTHER INFORMATION: FRI3' Primer

<400> SEQUENCE: 49
cgtaaccgcg ggcatgcgct agcaagcttt gcgcataact ggttcaggac cacgga        56

<210> SEQ ID NO 50
<211> LENGTH: 32
<212> TYPE: DNA
<213> ORGANISM: Artificial
<220> FEATURE:
<223> OTHER INFORMATION: FRII 5' Primer

<400> SEQUENCE: 50
cctatgcatg ctgcacagaa tccttggtga ac        32

<210> SEQ ID NO 51
<211> LENGTH: 33
<212> TYPE: DNA
<213> ORGANISM: Artificial
<220> FEATURE:
<223> OTHER INFORMATION: FRII 5' Primer

<400> SEQUENCE: 51
cctataagct tggtgaacag gcgaccatgc ttt        33

<210> SEQ ID NO 52
<211> LENGTH: 9
<212> TYPE: DNA
<213> ORGANISM: Artificial
<220> FEATURE:
<223> OTHER INFORMATION: Hind III cloning site of FRII5'-2 primer before
      change

<400> SEQUENCE: 52 gaatccttg        9

```
<210> SEQ ID NO 53
<211> LENGTH: 9
<212> TYPE: DNA
<213> ORGANISM: Artificial
<220> FEATURE:
<223> OTHER INFORMATION: Hind III cloning site of FRII5'-2 primer after
      change

<400> SEQUENCE: 53 gaaagcttg                                                              9

<210> SEQ ID NO 54
<211> LENGTH: 56
<212> TYPE: DNA
<213> ORGANISM: Artificial
<220> FEATURE:
<223> OTHER INFORMATION: FRI3' primer

<400> SEQUENCE: 54
cgtaaccgcg ggcatgcgct agcaagcttt gcgcagcact tctctacaaa agctgc         56

<210> SEQ ID NO 55
<211> LENGTH: 126
<212> TYPE: DNA
<213> ORGANISM: Artificial
<220> FEATURE:
<223> OTHER INFORMATION: HSA II fragment

<400> SEQUENCE: 55
ctttgccgag gagggtaaaa agcttgttgc tgcaagtcaa gctgccttag gcttatagcc     60
gcgtacgaaa cggctcctcc cattttttcga acaacgacgt tcagttcgac ggaatccgaa   120
tatcgg                                                               126

<210> SEQ ID NO 56
<211> LENGTH: 10
<212> TYPE: DNA
<213> ORGANISM: Artificial
<220> FEATURE:
<223> OTHER INFORMATION: Hind III site of pPICZ(alpha)A before change

<400> SEQUENCE: 56
caagcttgtt                                                            10

<210> SEQ ID NO 57
<211> LENGTH: 10
<212> TYPE: DNA
<213> ORGANISM: Artificial
<220> FEATURE:
<223> OTHER INFORMATION: Hind III site of pPICZ(alpha)A after change

<400> SEQUENCE: 57
caagcatgtt                                                            10

<210> SEQ ID NO 58
<211> LENGTH: 9
<212> TYPE: PRT
<213> ORGANISM: Artificial
<220> FEATURE:
<223> OTHER INFORMATION: Peptide faTraE

<400> SEQUENCE: 58

Cys His Leu Asp Ala His Trp Lys Gly
1               5
```